United States Patent
Deev et al.

(10) Patent No.: US 11,992,581 B2
(45) Date of Patent: May 28, 2024

(54) METHODS OF PRODUCING OPTIMIZED GENE-ACTIVATED MATERIALS

(71) Applicant: HISTOGRAFT, LLC, Moscow (RU)

(72) Inventors: Roman Vadimovich Deev, St. Petersburg (RU); Artur Aleksandrovich Isaev, Moscow (RU); Ilya Yadigerovich Bozo, Kuvshinovo (RU); Vladimir Sergeevich Komlev, Moscow (RU)

(73) Assignee: HISTOGRAFT, LLC, Moscow (RU)

( * ) Notice: Subject to any disclaimer, the term of this patent is extended or adjusted under 35 U.S.C. 154(b) by 600 days.

(21) Appl. No.: 16/376,552

(22) Filed: Apr. 5, 2019

(65) Prior Publication Data

US 2019/0224379 A1 Jul. 25, 2019

Related U.S. Application Data

(63) Continuation of application No. PCT/RU2017/000455, filed on Jun. 27, 2017.

(30) Foreign Application Priority Data

Oct. 7, 2016 (RU) ............................ RU2016139396

(51) Int. Cl.
| | |
|---|---|
| *A61L 27/54* | (2006.01) |
| *A61K 48/00* | (2006.01) |
| *A61L 27/12* | (2006.01) |
| *A61L 27/18* | (2006.01) |
| *A61L 27/36* | (2006.01) |
| *A61L 27/46* | (2006.01) |
| *C12Q 1/6834* | (2018.01) |

(52) U.S. Cl.
CPC .............. *A61L 27/54* (2013.01); *A61K 48/00* (2013.01); *A61L 27/12* (2013.01); *A61L 27/18* (2013.01); *A61L 27/3608* (2013.01); *A61L 27/46* (2013.01); *C12Q 1/6834* (2013.01); *A61L 2300/414* (2013.01); *A61L 2430/02* (2013.01)

(58) Field of Classification Search
CPC .. A61L 2400/12; A61L 2430/22; A61L 27/26; A61L 27/50; A61L 2430/02; A61L 27/3608; A61L 27/54; A61L 27/12; A61L 27/18; A61L 27/46; A61L 2300/258; C08L 75/04; D01D 5/0076; Y10T 428/1362; A61K 48/00; C12Q 1/6834
See application file for complete search history.

(56) References Cited

U.S. PATENT DOCUMENTS

2009/0238879 A1*  9/2009  Shea ........................ A61L 27/26
424/93.1
2014/0341870 A1*  11/2014  Isaev ........................ A61L 27/54
424/93.21

OTHER PUBLICATIONS

Geiger et al. (J. Funct. Biomater, 2012, 3, 313-326). (Year: 2012).*
Sokolova et al.—"Effective transfection of cells with multi-shell calcium phosphate-DNA nanoparticles", Biomaterials 27 (2006), pp. 3147-3153.
Hanifi et al.—"Mg2+ substituted calcium phosphate nano particles synthesis for non viral gene delivery application", J. Mater. Sci: Mater Med (2010) 21, pp. 2393-2401.
Bang et al.—"Autologous Mesenchymal Stem Cell Transplantation in Stroke Patients", Annals of Neurology, vol. 57, No. 6, Jun. 2005.
Deev et al.—"pCMV-vegf165 Intramuscular Gene Transfer is an Effective Method of Treatment for Patients with Chronic Lower Limb Ischemia"(2015).
Suh—"Tissue Restoration, Tissue Engineering and Regenerative Medicine", Yonsei Medical Journal, vol. 41, No. 6, pp. 681-684, 2000.
Tatara et al.—"Tissue Engineering in Orthopaedics", The Journal of Bone & Joint Surgery (jbjs.org), vol. 98-A, No. 13, Jul. 6, 2016, pp. 1132-1139.
Chang et al.—"Dual delivery of PDGF and simvastatin to accelerate periodontal regeneration in vivo", Biomaterials 34 (2013), pp. 9990-9997.
Holloway et al.—"Modulating Hydrogel Crosslink Density and Degradation to Control Bone Morphogenetic Protein Delivery and In Vivo Bone Formation", J. Control Release, Oct. 10, 2014, 191, pp. 63-70.
Zhang et al.—"VEGF and BMP-2 Promote Bone Regeneration by Facilitating Bone Marrow Stem Cell Homing and Differentiation", European Cells and Materials vol. 27, 2014 (pp. 1-12). www.ecmjournal.org.
Eastlack et al.—"Osteocel Plus Cellular Allograft in Anterior Cervical Discectomy and Fusion", Spine vol. 39, No. 22, pp. E1331-E-1337, www.spinejournal.com (2014).
Kim et al.—"Improvements of osteoblast adhesion, proliferation, and differentiation in vitro via fibrin network formation in collagen sponge scaffold", Journal of Biomedical Materials Research Part A, (2013), 6 pages.
Pelegrine et al.—"Repair of critical-size bone defects using bone marrow stromal cells: a histomorphometric study in rabbit calvaria. Part I: Use of fresh bone marrow or bone marrow mononuclear fraction", Clin. Oral Impl. Res. 25. 2014, pp. 567-572.
Illich et al.—"Concise Review: Induced Pluripotent Stem Cells and Lineage Reprogramming: Prospects for Bone Regeneration", Stem Cells 2011; 29, pp. 555-563.
Wegman et al.—"Osteogenic Differentiation as a Result of BMP-2 Plasmid DNA Based Gene Therapy in vitro and in vivo", European Cells and Materials vol. 21, 2011 (pp. 230-242).

(Continued)

*Primary Examiner* — Anna R Falkowitz
(74) *Attorney, Agent, or Firm* — Oblon, McClelland, Maier & Neustadt, L.L.P.

(57) ABSTRACT

Provided are gene-activated materials comprising a scaffold and at least one nucleic acid molecule which may be chemical bound together or in which the at least one nucleic acid is not bound but coated on a surface of the scaffold. Methods for regenerating bone using these gene-activated materials are also provided.

11 Claims, 9 Drawing Sheets
(9 of 9 Drawing Sheet(s) Filed in Color)

(56) References Cited

OTHER PUBLICATIONS

Kleinschmidt et al.—"Enhanced reconstruction of long bone architecture by a growth factor mutant combining positive features of GDF and BMP-2", Biomaterials 34 (2013), pp. 5926-5936.

Zorin et al.—"Octacalcium phosphate ceramics combined with gingiva-derived stromal cells for engineered functional bone grafts", Biomed. Mater. 9(2014), 055005, 12 pages.

Knight et al.—"Mesenchymal Stem Cells in Bone Regeneration", Advances in Wound Care, vol. 2, No. 6, pp. 306-316 (2013).

Kan et al.—"Integral Therapeutic Potential of Bone Marrow Mesenchymal Stem Cells", Current Drug Targets, 2005, 6, pp. 31-41.

Huang et al.—"Combined Angiogenic and Osteogenic Factor Delivery Enhances Bone Marrow Stromal Cell-Driven Bone Regeneration", Journal of Bone and Mineral Research, vol. 20, No. 5, 2005, pp. 848-857.

Jahani et al.—"Controlled surface morphology and hydrophilicity of polycaprolactone toward selective differentiation of mesenchymal stem cells to neural like cells", Journal of Biomedical Materials Research A, 2014, 7 pages.

Motamedian et al.—"Smart scaffolds in bone tissue engineering" A systematic review of literature, World J Stem Cells, Apr. 26, 2015,7(3), pp. 657-668.

He et al.—"Surface Modification of PLLA Nano-scaffolds with Laminin Multilayer by LbL Assembly for Enhancing Neurite Outgrowth", Macromol. Biosci. 2013, 13, pp. 1601-1609.

Shim et al.—"A study of a three-dimensional PLGA sponge containing natural polymers co-cultured with endothelial and mesenchymal stem cells as a tissue engineering scaffold", Biomed. Mater. 9 (2014), 045015, 10 pages.

Liu et al.—"Vascularized Bone Tissue Formation Induced by Fiber-Reinforced Scaffolds Cultured with Osteoblasts and Endothelial Cells", BioMed Research International, vol. 2013, Article ID 854917, 7 pages, Accepted Nov. 13, 2013.

Li et al.—"Guided bone regeneration using chitosan/collagen membranes in dog dehiscence-type defect model", Journal of Oral and Maxillofacial Surgery (2013), 34 pages.

Lanao et al.—"Physicochemical Properties and Applications of Poly(lactic-co-glycolic acid) for Use in Bone Regeneration", Tissue Engineering: Part B, vol. 19, No. 4, 2013, pp. 380-390.

Wang et al.—"Bioactive and biodegradable silica biomaterial for bone regeneration", Bone 67 (2014), pp. 292-304.

Zakaria et al.—"Nanophase Hydroxyapatite as a Biomaterial in Advanced Hard Tissue Engineering: A Review", Tissue Engineering: Part B, vol. 19, No. 5, 2013, pp. 431-441.

Komlev et al.—"Bioceramics Composed of Octacalcium Phosphate Demonstrate Enhanced Biological Behavior", ACS Applied Materials & Interfaces 2014, 6, pp. 16610-16620.

Yu et al.—"Decellularized scaffolds in regenerative medicine", www.impactjournals.com/oncotarget, Oncotarget, vol. 7, No. 36, pp. 58671-58683 (2016).

Deev et al.—"Ordinary and Activated Bone Grafts: Applied Classification and the Main Features", BioMed Research International, vol. 2015, Article ID 365050, 19 pages, accepted Oct. 15, 2015.

Sadri-Ardekani et al., "Regenerative medicine", Methods 99 (2016), pp. 1-2.

De Cicco et al.—"Prilling and Supercritical Drying: a Successful Duo to Produce Core-Shell Polysaccharide Aerogel Beads for wound healing", Carbohydrate Polymers, 25 pages (2016).

Sabri et al.—"Novel Technique for Repair of Severed Peripheral Nerves in Rats Using Polyurea Crosslinked Silica Aerogel Scaffold", Journal of Investigative Surgery, Early Online 2014, pp. 1-10.

Andreev et al.—"Efficacy of Dermoplasty and the Dermal Equivalent in Treatment of Vast Leg Ulcers of Mixed Genesis". Department of faculty surgery of the State Pavlov Medical University; Department of cell cultures of the Institute of Cytology of the Russian Academy of Sciences (with English abstract), pp. 104-107 (2013).

Duguid et al.—"Raman Spectroscopy of DNA-Metal Complexes. I. Interactions and Conformational Effects of the Divalent Cations: Mg, Ca, Sr, Ba, Mn, Co, Ni, Cu, Pd, and Cd1" Biophysical Journal vol. 65, Nov. 1993, pp. 1916-1928.

Graham et al.—"Transformation of Rat Cells by DNA of Human Adenovirus 5", Virology 54, (1973), pp. 536-539.

Zhang et al.—"Magnesium modification of a calcium phosphate cement alters bone marrow stromal cell behavior via an integrin-mediated mechanism", Biomaterials 53 (2015), pp. 251-264.

Evans—"Gene delivery to bone", Advanced Drug Delivery Reviews 64, (2012), pp. 1331-1340.

Bozo et al.—"Efficacy of Gene-Activated Osteoplastic Material Based on Octacalcium Phosphate and Plasmid DNA containing vegf Gene for Critical-sized Bone Defects Substitution" Human Stem Cells Institute, Moscow; A.I. Evdokimov Moscow State University of Medicine and Dentistry, Moscow; A.I. Burnazyan Federal Medical and Biophysical Center, Moscow; Kazan (Volga region) Federal University, Kazan; A. A. Baikov Institute of Metallurgy and Materials Science, Moscow; I.M. Sechenov First Moscow State Medical University, Moscow; X-ray Diagnostics Laboratories 3D Lab, Moscow, Russia. (English abstract), 2015, No. 1.

Giovannini et al.—"Comparison of different types of ceramic hydroxyapatite for the chromatographic separation of plasmid DNA and a recombinant anti-Rhesus D antibody", Bioseparation 9, pp. 359-368, 2001.

Keeney et al.—"The ability of a collagen/calcium phosphate scaffold to act as its own vector for gene delivery and to promote bone formation via transfection with $VEGF_{165}$" Biomaterials 31 (2010), pp. 2893-2902.

Grigorian et al.—"Some possible molecular mechanisms of VEGF encoding plasmids functioning", Human Stem Cells Institute, Moscow, No. 3, 2011.

Baboo et al.—""Dark matter" worlds of unstable RNA and protein", Nucleus, 5:4, pp. 281-286 , DOI: 104161/nucl.29577, Jun. 20, 2014.

Lu et al.—"Porous Chitosan Scaffolds with Embedded Hyaluronic Acid/Chitosan/Plasmid-DNA Nanoparticles Encoding TGF-β1 Induce DNA Controlled Release, Transfected Chondrocytes, and Promoted Cell Proliferation", PLOS One, Jul. 2013, vol. 8, Issue 7 (13 pages).

Rose et al.—"Treatment of critically sized defects and enhancement of fracture healing in an osteoporotic animal model based on ex vivo gene therapy using BMP4", published Nov. 4, 2004, 10 pages (English abstract).

\* cited by examiner

METHODS OF PRODUCING OPTIMIZED GENE-ACTIVATED MATERIALS

CROSS-REFERENCE TO RELATED APPLICATIONS

This application is a continuation of PCT/RU2017/000455, filed Jun. 27, 2017, which claims priority to RU 2016139396, filed Oct. 7, 2016; both of which are incorporated by reference in their entireties.

BACKGROUND OF THE INVENTION

Field of the Invention

The invention pertains to gene-activated material and methods of using it for tissue regeneration.

Description of Related Art

The prevalence of diseases and pathological conditions, accompanied or leading to human tissue and organ injuries, is extremely high. The primary causes of bone and musculoskeletal injuries, skin, subcutaneous tissue, mucous membranes, vessels, peripheral nerves and internal organs are traumas, oncological, inflammatory and degenerative-dystrophic diseases, congenital disorders and deformations including first stages of their surgical treatment.

Traumas hold a leading place within the structure of causes of tissue and organ injuries. According to WHO, the annual number of victims of road traffic accidents is 30-50 million people. See Road traffic accident injuries, Information letter, May 2016. Hypertext transfer protocol available on the World Wide Web at who.intymediacentre/factsheets/fs358/ru/, incorporated herein by reference in its entirety. In Russia, according to State Road Safety Inspectorate, about 230 thousand people get injured as a result of road traffic accidents. See Information about road traffic safety indicators. Hypertext transfer protocol available at World Wide Web gibdd.ru/stat, incorporated herein by reference in its entirety. In regard to oncological diseases, according to WHA forecast, the annual number of newly diagnosed cases will increase from 14 million in 2012 up to 22 million by 2020. See Cancer. Information letter N° 297, February 2015, Hypertext transfer protocol available on the World Wide Web at who.int/mediacentre/factsheets/fs297/ru/, incorporated herein by reference in its entirety.

As a result, the annual number of patients, requiring reconstructive surgeries, is extremely high. The effective treatment of major cases may be achieved by application of standard methods and techniques, but for a considerable part of patients it is still impossible to obtain successful results and restore the initial quality of life. It is caused by the fact, that in case of large (extensive) tissue and organ injuries, with presence of comorbidity and risk factors, confounding a clinical situation, within the defect zone a number of cambial cells and biologically active substances, inducing reparative regeneration of tissues, is minimized, thus, making it impossible to achieve complete histotypic recovery. The effective treatment in such cases may be provided using only those methods and techniques, that have an impact on reparative regeneration of tissues, compensate lost structures and cambial reserve and introduce factors, regulating recovery process, etc. Actually, understanding of this situation became the background for so-called "regenerative medicine" formation. See Suh H. Tissue restoration, tissue engineering and regenerative medicine. Yonsei Med J. 2000 December; 41(6):681-4, incorporated herein by reference in its entirety.

Within the frame of regenerative medicine active research and development of new biopharmaceuticals are performed (gene, cellular), medical products and devices, that may have a significant effect on reparative regeneration of tissues, regenerate the lost structure and function of injured organs and make it possible to perform their partial and even complete replacement (personalized technologies using three-dimensional printing). See Deev R V, Bozo I Y, Mzhavanadze N D, Voronov D A, Gavrilenko A V, Chervyakov Y V, Staroverov I N, Kalinin R E, Shvalb P G, Isaev A A. pCMV-vegfl65 Intramuscular Gene Transfer is an Effective Method of Treatment for Patients With Chronic Lower Limb Ischemia. J Cardiovasc Pharmacol Ther. 2015 September; 20(5):473-82; Bang O Y, Lee J S, Lee P H, Lee G. Autologous mesenchymal stem cell transplantation in stroke patients. Ann Neurol. 2005 June; 57(6):874-82; Tatara A M, Mikos A G. Tissue Engineering in Orthopaedics. J Bone Joint Surg Am. 2016 Jul. 6; 98(13): 1132-9; and Sadri-Ardekani H, Atala A. Regenerative medicine. Methods. 2016 Apr. 15; 99:1-2, each incorporated herein by reference in their entirety.

A wide range of tools of cellular, gene and post-genomic technologies has been formed in regenerative medicine. Living cells, growth factors, gene constructs, separately and in various combinations, both without additional elements and within the composition of various scaffolds are developed and evaluated by their safety and efficiency for regeneration of injured tissues and organs. See Sadri-Ardekani et al. (2016); and Deev R. V., Drobyshev A. Y., Bozo I. Y., Isaev A. A. Ordinary and Activated Bone Grafts: Applied Classification and the Main Features. Biomed Res Int. 2015; 2015:365050, each incorporated herein by reference in their entirety.

Various materials are used as scaffolds, primarily, bioresorbable ones, without biologically active components in their composition, standardized by qualitative and quantitative parameters. Scaffold material may be obtained from an autologous, allogenic or xenogenic source, or may be artificial. The main materials are as follows: allogenic and xenogeneic matrices, processed by means of various technologies (decellularization, demineralization, deproteinization, etc.); inorganic compounds of β-tricalcium phosphate, octacalcium phosphate (OCP), natural or synthetic hydroxyapatite, silicates, etc.); synthetic (PLGA, agarose, etc.) and natural (collagen, chitosan, gelatine, sodium alginate) organic substances, polymers and organic acid salts, and also composite products of the above mentioned materials. Matrix carriers may be solid substance, gel (including hydrogels) and aerogels. See Yu Y, Alkhawaji A, Ding Y, Mei J. Decellularized scaffolds in regenerative medicine. Oncotarget. 2016 Jul. 29. doi: 10.18632/oncotarget. 10945. [Epub ahead of print]; Wang Z., Guo Z., Bai H. et al. Clinical evaluation of β-TCP in the treatment of lacunar bone defects: a prospective, randomized controlled study. Mater. Sci. Eng. C Mater. Biol. Appl. 2013; 33(4): 1894-9; Komlev V. S., Barinov S. M., Bozo I. I. et al. Bioceramics composed of octacalcium phosphate demonstrate enhanced biological behaviour. ACS Appl. Mater. Interfaces 2014; 6(19): 16610-20; Zakaria S. M., Sharif Zein S. H., Othman M. R. et al. Nanophase hydroxyapatite as a biomaterial in advanced hard tissue engineering: a review. Tissue Eng. Part B Rev. 2013; 19(5): 431-41; Wang S., Wang X., Draenert F. G. et al. Bioactive and biodegradable silica biomaterial for bone regeneration. Bone 2014; 67: 292-304; Felix Lanao R. P., Jonker A. M., Wolke J. G. et al. Physicochemical properties and applications of poly(lactic-co-glycolic acid) for .use in bone regeneration. Tissue Eng. Part B Rev. 2013; 19(4): 380-90; Li X., Wang X., Miao Y., Yang G. et al. Guided bone regeneration at a dehiscence-type defect using chitosan/collagen membranes in dogs. Zhonghua Kou Qiang Yi Xue Za Zhi. 2014; 49(4): 204-9; Sabri F, Gerth D, Tamula G R et al. Novel technique for repair of severed peripheral nerves in rats using polyurea crosslinked silica aerogel scaffold. J Invest Surg. 2014; 27(5):294-303; and De Cicco F, Russo P, Reverchon E, et al. Prilling and supercritical drying: A successful duo to produce core-shell polysaccharide aerogel beads for wound healing. Carbohydr Polym. 2016; 147:482-9, each incorporated herein by reference in its entirety.

Most matrices without biologically active components have only optimizing effect on the reparative regeneration of tissues, but they are not able to activate it and maintain on high level until complete histotypic healing. In other words, they perform only mechanical function (defect zone compensation, direction of forming tissues from the defect edges to the centre) and can also supply biologically active substances, preliminarily introduces into the material. See Deev et al. (2015). The main directions of scaffolds improvement are as follows: composition optimization (by means of combination of several substances including), surface modification by means of treatment with substances, improving attachment of biologically active components (cells, proteins, gene structures), and by means of the surface macro- and microrelief change, nanostructuring, thus, making it possible to modulate the function of cells, integrated with matrices prior to introduction in vivo and (or) host bed cells. See He L, Tang S, Prabhakaran M P, Liao S, Tian L, Zhang Y, Xue W, Ramakrishna S. Surface modification of PLLA nano-scaffolds with laminin multilayer by LbL assembly for enhancing neurite outgrowth. Macromol Biosci. 2013 November; 13(11):1601-9; Motamedian S R, Hosseinpour S, Ahsaie M G, Khojasteh A. Smart scaffolds in bone tissue engineering: A systematic review of literature. World J Stem Cells. 2015 Apr. 26; 7(3):657-68; and Jahani H, Jalilian F A, Wu C Y, et al. Controlled surface morphology and hydrophilicity of polycaprolactone toward selective differentiation of mesenchymal stem cells to neural like cells. J Biomed Mater Res A. 2015 May; 103(5): 1875-81, each incorporated herein by reference in their entirety.

Earlier, our research team developed the biocomposite, consisting of the scaffold, plasmid DNA, carrying genes vegf and (or) sdf, and cells, involved in reparative regeneration of tissues. See Patent biocomposite, incorporated herein by reference in its entirety. Other researchers decided on a complex four-component system, represented by the scaffold, cells, gene constructs and growth factors. See Huang Y C, Kaigler D, Rice K G et al. Combined angiogenic and osteogenic factor delivery enhances bone marrow stromal cell-driven bone regeneration. J Bone Miner Res. 2005 May; 20(5):848-57, incorporated herein by reference in its entirety. The basic prerequisite for development of such biocomposites was caused by unsatisfactory result of two-component systems: "scaffold+cells", "scaffold+growth factors", "scaffold+gene constructs".

Tissue-engineered materials. This group of material is represented by the products, consisting of two main components: a bioresorbable scaffold and living (auto- or allogenic) cells. The main idea of this approach lies in compensation of lost cambial reserves and enhancement of factors, inducing reparative process in the zone of material implantation. Transplanted cells in the host bed, if they preserve a viability, may have a favorable therapeutic effect by means of two mechanisms of action: direct effect—differentiation to the target cells of injured tissues (well-known for autogenic cells)), and mediated—paracrine effect—regulation of morphofunctional activity of other cells by means of production of biologically active substances—factors of histogenesis local regulation. It is important, that many authors consider paracrine activity of cells of tissue engineered materials to be the main mechanism of action. See Kan I., Melamed E., Offen D. Integral therapeutic potential of bone marrow mesenchymal stem cells. Curr. Drug Targets. 2005; 6(1): 31-41; and Knight M. N., Hankenson K. D. Mesenchymal Stem Cells in Bone Regeneration. Adv. Wound Care (New Rochelle). 2013; 2(6): 306-16, each incorporated herein by reference in their entirety.

The cells, used for production of tissue engineered materials, may be cultured or used directly after extraction from the tissue source. The main types of cultured cells, used for production of tissue-engineered materials, include multipotent mesenchymal stromal cells (MMSC), osteogenic cells and osteoblasts, endotheliocytes, fibroblasts, epitheliocytes, induced pluripotent stem cells and other types of poorly differentiated and target cells, both separately and in various combinations. See Zorin V. L., Komlev V. S., Zorina A. I. et al. Octacalcium phosphate ceramics combined with gingiva-derived stromal cells for engineered functional bone grafts. Biomed. Mater. 2014; 9(5): 055005; Deev R. V., Isaev A. A., Kochish A. Yu. et al. Development patterns of cellular technologies in orthopedic surgery. Traumatology and Orthopedics of Russia 2008; 1(47): 65-75; Liu X., Zhang G., Hou C. et al. Vascularized bone tissue formation induced by fiber-reinforced scaffolds cultured with osteoblasts and endothelial cells. Biomed. Res. Int. 2013; 2013: 854917; Kim B. S., Kim J. S., Lee J. Improvements of osteoblast adhesion, proliferation, and differentiation in vitro via fibrin network foimation in collagen sponge scaffold. J. Biomed. Mater. Res. A. 2013; 101(9): 2661-6; Lu Y. M., Cheng L. M., Pei G. X. et al. Experimental study of repairing femoral bone defects with nHA/RHLC/PLA scaffold composite with endothelial cells and osteoblasts in canines. Zhonghua Yi Xue Za Zhi. 2013; 93(17): 1335-40; Shim J. B., Ankeny R. F., Kim H. et al. A study of a three-dimensional PLGA sponge containing natural polymers co-cultured with endothelial and mesenchymal stem cells as a tissue engineering scaffold. Biomed. Mater. 2014; 9(4): 045015; Andreev D I, Abramova N V, Blinova M I, Pinaev G P. Efficacy of dermoplasty and the dermal equivalent in treatment of vast leg ulcers of mixed genesis. Vestn Khir Im I 1 Grek. 2013; 172(1): 104-7; and Mich D. J., Demir N., Stojkovic M. et al. Concise review: induced pluripotent stem cells and lineage reprogramming: prospects for bone regeneration. Stem Cells 201 1; 29(4): 555-63, each incorporated herein by reference in their entirety. Non-cultured cell populations include bone marrow cells ("heterogeneous mixture" of MMSC, fibroblasts, endothelial progenitor cells, hematopoietic stem and definitive cells of hematopoietic line, etc.) and stromal-vascular fraction of fat tissue (SVF FT) (MMSC, endotheliocytes and endothelial progenitor cells, leiomyocytus, fibroblasts, preadipocytes and immune competent cells). See Pelegrine A. A., Aloise A. C., Zimmermann A. et al. Repair of critical-size bone_defects using bone marrow stromal cells: a histomorphometric study in rabbit calvaria. Part I: use of fresh bone marrow or bone marrow mononuclear fraction. Clin. Oral. Implants Res. 2014; 25(5): 567-72; and Kim B. S., Kim J. S., Lee J. Improvements of osteoblast adhesion, proliferation, and differentiation in vitro via fibrin network formation in collagen sponge scaffold. J. Biomed. Mater. Res A. 2013; 101(9): 2661-6, each incorporated herein by reference in their entirety.

Production of tissue-engineered materials with allogenic cells may be performed using fundamentally new technologies, involving conservative treatment of tissue donors with preservation of components of intracellular matrix and living cells. See Eastlack R K, Garfm S R, Brown C R, Meyer S C. Osteocel Plus cellular allograft in anterior cervical discectomy and fusion: evaluation of clinical and radiographic outcomes from a prospective multicenter study. Spine (Phila Pa. 1976). 2014 Oct. 15; 39(22):E133 1-7, incorporated herein by reference in its entirety.

Despite the fact, that some tissue-engineered products have already been registered and approved for use in routine clinical practice ("Osteocel plus" (NuVasive, USA) (2005), "Trinity Evolution" (Orthofix, USA) (2009), "AlloStem" (AlloSource) (2011), "Cellentra VCBM" (BioMet, USA) (2012), "OvationOS" (Osiris Therapeutics, USA) (2013), "BioSeed-Oral Bone" (BioTissue Technologies, Germany) (2001)), this approach has a number of disadvantages:

insufficient efficiency in case of tissue and organ large defects due to death of most cells constituting the tissue-engineered material right after transplantation, because tissue-engineered products without prefabrication are avascular, when cells require active blood supply, which is critically minimized within the damage zone;

high cost and complexity of technological process (cellular service) of tissue-engineered material production to be performed according to standards GMP and GTP;

impossibility to organize complete series production of the most efficient, personalized (containing autogenic cells) tissue-engineered products; special storage conditions, that are not always available for health care facilities (for example, temperature below −80° C.); and continued difficulties of legal regulation and registration of medical products, containing cells.

Materials with growth factors. This group of medical products includes materials, consisting of a scaffold and growth factors (one or several), providing regulation of reparative regeneration of tissues. This technological approach is the most successful in the aspect of the "clinical translation". The following products have already been registered and approved for clinical use: "Emdogain" (Straumann, Germany)—material with enamel matrix proteins (1997); "OP-1" (Stryker Biotech, USA)—with recombinant BMP-7 (2001); "Infuse" (Medtronic, USA) (2002, 2004, 2007)—with recombinant BMP-2; "GEM21 S", "Augment bone graft" (BioMimetic Therapeutics Inc., USA)—with recombinant PDGF-BB (2005, 2009), "i-Factor Putty" (Cerapedics, USA)—with protein P-15 (ligand for integrins $\alpha 2\beta 1$, expressed by cells of osteoblastic programmed differentiation) (2008), etc.

The advanced research and developments of materials with growth factors are aimed at two main aspects. The first one involve a combination of several, including non-specific (angiogenic) and specific (with selective effect on the certain mechanism in the whole process of reparative regeneration of some tissue) factors within one product. For example, immobilization VEGF and BMP-2 on one scaffold. See Zhang W., Zhu C, Wu Y. et al. VEGF and BMP-2 promote bone regeneration by facilitating bone marrow stem cell homing and differentiation. Eur. Cell Mater. 2014; 27: 1-11, incorporated herein by reference in its entirety. The second one ensure prolonged controlled release of therapeutic proteins from the matrix structure, in particular, by control of dynamics of hydrogel matrix biodegradation or incapsulation of molecules of growth factors into microspheres from organic polymers. See Holloway J. L., Ma H., Rai R. et al. Modulating hydrogel crosslink density and degradation to control bone morphogenetic protein delivery and in vivo bone formation. J. Control. Release. 2014; 191:63-70; and Chang P. C., Dovban A. S., Lim L. P. et al. Dual delivery of PDGF and simvastatin to accelerate periodontal regeneration in vivo. Biomaterials 2013; 34(38): 9990-7, each incorporated herein by reference in their entirety. Some authors, using special technologies (for example, site-directed mutagenesis) change the structure of growth factors, combine several factors into one, forming "mutant" molecules, having a higher efficiency in reparative process activation. For example, P. Kasten et al (2010) modified the growth factor and differentiation-5 (growth-and-differentiation factor-5, GDF-5) by adding in its sequence sites BMP-2, responsible for binding with specific receptors. As a result, the obtained molecule GDF-5 acquired properties typical for BMP-2. See Kleinschmidt K., Ploeger F., Nickel J. et al. Enhanced reconstruction of long bone architecture by a growth factor mutant combining positive features of GDF-5 and BMP-2. Biomaterials 2013; 34(24): 5926-36, incorporated herein by reference in its entirety.

But two-component biocomposite, consisting of a scaffold and growth factors, also have a number of disadvantages, limiting their efficiency. First, protein molecules in the conditions of surgical wound (exudation, high activity of proteolytic enzymes) are subject to fast biodegradation and are short-living and short-distant, thus, not allowing the material to reveal its inducing action in full. Second, the amount of therapeutic protein in the material is limited and its action is short-term and "rough" even in case of controlled and prolonged release. In other words, the less part of protein molecules, that released from the scaffold, preserved its biological activity and reached the target cells, will interact with specific receptors on their surface and cause biological effect. At this, inactivation of receptors will occur soon together with the ligand as a compensatory and adaptation mechanism, protecting cells from excessive stimulation, biological action of growth factors will stop and its amount will run out. This aspect of mechanism of such materials has quite a negative effect on their efficiency with absence of the specified kinetics of growth factor release (which is typical for mot products of this group). Right after implantation the sequential change of early stage of inflammatory process occurs (alteration, then exudation), when the growth factors, released from the material, that i, regulators of reparative regeneration, are not required. Moreover, at this early (first) stage of reparative process for growth factors from the implanted material composition may not be sufficient receptive field, as the main cells in the injury zone will be immune competent cells, that is, neutrophils and macrophages. The third alternative approach is free of such disadvantages.

Gene-activated materials. This group of materials is represented by a complex of "matrix carrier+gene structures (coding nucleic acids)", with its components combined by using various methods: by technologies of "chemical bonding", use of auxiliary substances (for example, gel biopolymers), direct inclusion of nucleic acids in the carrier composition at the stage of matrix synthesis, etc. See Deev R. V., Drobyshev A. Yu., Bozo I. Ya. et al. Development and evaluation of biological effect of the gene-activated osteoplastic material, carrying human VEGF gene. Cellular Transplantation and Tissue Engineering 2013; VIII (3):

78-85; and Wegman F., Bijenhof A., Schuijff L. et al. Osteogenic differentiation as a result of BMP-2 plasmid DNA based gene therapy in vitro and in vivo. Eur. Cell Mater. 2011; 21: 230-42, each incorporated herein by reference in their entirety. The development of gene-activated materials is directly related to achievements of gene therapy as a whole; within its frame gene structure are developed as active substances of gene-therapeutic medical products.

Within the mechanism of osteo-inductive action of gene-activated material two sequential stages may be singled out: non-specific and specific. The first one consists in release of nucleic acids from the carrier structure after implantation into the defect zone and introduction in cells of host bed and expression within them. Actually, it is the same for all gene structures, the variability in the aspect of its introduction in the cell is caused only by transgene supply systems. The second one consists in specific action of the protein regulatory molecule, coded by transgene and produced by transfected cells, acting as "bioreactors" of therapeutic protein, synthesizing it during the controlled period of time. Unlike products, containing growth factors, the main component of gene-activated bone substitute acts in a "gentle" way. In other words, the penetration of transgene in the target cell nucleus does not force it to obligatory expression of the therapeutic protein. The cell preserves its normal functional state, and with no demand of the therapeutic protein within the specific period of time, it, by means of intracellular post transcriptional mechanisms of mRNA half-life regulation mechanisms, may lower the level of mRNA transgene, thus, preventing protein production. See Baboo S., Cook P. R. "Dark matter" worlds of unstable RNA and protein. Nucleus 2014 Jun. 20; 5(4) [Epub ahead of print], incorporated herein by reference in its entirety. Besides, even without specified kinetic of gene structures release, their penetration in the host bed cells, further expression and the beginning of prolonged production of therapeutic protein requires time. At this, the protein secretion peak by transfected cells will take place at the second stage of reparative process, after completion of the inflammatory stage. This mechanism of gene structures considerable increase efficiency of gene-activated material compared to the products, containing growth factors. See Evans C. H. Gene delivery to bone. Adv. Drug Deliv. Rev. 2012; 64(12): 133 1-40, incorporated herein by reference in its entirety.

All gene structure consist of therapeutic gene (in the form of complementary DNA or RNA) and the system of its intracellular supply (vector). The vectors are divided in two main groups: viral and non-viral. In the first case the transgene is encapsulated in the particle of retro-, lenti-, adenovirus or adeno-associated virus, etc.; in the second case, it is encapsulated in the plasmid, a circular molecule of nucleic acid, containing a number of auxiliary sequences, providing transgene expression. Viral and non-viral systems of supply differ in transfection efficiency. In the first case up to 40% and more gene structures come to target cells, in the second case—the indicator does not exceed 1-2% due to sizes and negative charge of "naked" plasmid DNA. The approaches (physical, chemical) were proposed to increase efficiency of plasmid DNA transfection up to 8-10%. See Grigoryan A. S., Shevchenko K. G. Possible molecular mechanisms of plasmid structure functioning, containing gene VEGF. Cellular Transplantation and Tissue Engineering 2011; VI(3): 24-8, incorporated herein by reference in its entirety.

A number of viral vector (retro-, lentiviral, etc.) are integrated with the genome. In other word, transgene expression, they are carrying, is long-lasting, when others, including plasmid DNA, are not integrated in the genome that is why they are expressed temporarily, during 10-14 days. Retro- and lentiviral vector are more often used in gene-cell approach, when the cell culture is transfected ex vivo and after that it i combined with the matrix carrier. See Rose T., Peng H Usas A. et al. Ex vivo gene therapy with BMP-4 for critically sized defects and enhancement of fracture healing in an osteoporotic animal model. Unfallchirurg 2005; 108 (1): 25-34, incorporated herein by reference in its entirety.

All gene-activated materials can be divided by the technological variant of matrix and gene structure combination and also by the composition of the biologically active component: the type of vector and transgene, number of transgenes or various gene structures within the composition of each product. But the main differentiating feature, conditioning difference in biological effect of gene-activated materials is transgene. The most widely applied transgenes during formation of gene-activated materials are sequence of nucleotide, coding the main growth factors and transcriptional factors, involved in the positive regulation of the reparative process—induction of migration, proliferation, differentiation of cells, their synthesis of the components of histotypical intracellular matrix and biologically active substances. See Deev et al. (2015). Besides, as transgenes, sequences of nucleotides and coding proteins of cell receptors may be used (increase of receptive field increases the host bed cell susceptibility to boundary factors and substances, introduced externally), cytokines (interleukin, tumor necrosis factor $-\alpha$, etc.), hormone and hormone-like substances, that can improve tissue regeneration.

But gene-activated materials and their manufacturing technologies, developed for now, have many specific disadvantages.

First, non-viral gene structures, included in the composition of gene-activated materials, are characterized by extremely low transfection efficiency, and use of physical (electrophoresis, ultrasound, etc.) or chemical (combination with cation proteins, liposomes, etc.) methods of increase of the level of biologically active substance penetration in cells is not always possible. Due to this fact, the researches have to use high dose of gene structures to increase the amount of accepting cells and achieve the desired biological effect. The increase of dose leads to increase in the product cost and may compromise its safety. Besides, technologies of gene-activated material development, based on formation of chemical bonds between the matrix carrier and nucleic acids does not always allow to increase the dose of gene structures, as such increase requires change of the matrix composition.

Second, the beginning of the transgene expression after implantation of the material in vivo is late for many gene-activated materials, that is, it occurs at the second stage of reparative process, after completion of inflammatory stage (in 2 weeks after introduction in vivo), the maximum level of transgene production falls for even later periods, depending on the kinetics of gene structure release from the matrix carrier. But gene-activated materials are not able to initiate earlier expression of gene structures and provide shift of time, required to achieve the maximum level of production of the therapeutic protein to the "left". To achieve this, various methods of gene-activated materials optimization are being developed, aimed at change and "programming" of the kinetics of biologically active component release from the matrix carrier structure. The most known methods are represented by encapsulation of nucleic acids molecules with further binding of complexes with the matrix carrier by the expense of mediators, sensitive to some factors (temperature, pH, ultrasound, specific ferments). The gradual destruction of the substance, providing binding of microcapsules or other complexes, containing nucleic acid, with the matrix carrier, provide controlled release of gene structures. See Lu H, Lv L, Dai Y, Wu G, Zhao H, Zhang F. Porous chitosan scaffolds with embedded hyaluronic acid/chitosan/plasmid-DNA nanoparticles encoding TGF-βI induce DNA controlled release, transfected chondrocytes, and promoted cell proliferation. PLoS One. 2013 Jul. 23; 8(7):e69950, incorporated herein by reference in its entirety.

Third, as it was mentioned above, in case, when combination of the scaffold and nucleic acids is perfoiiiied by chemical interaction of the specified components, the accuracy of gene structure dose is practically impossible to control. This disadvantage is particularly typical for solid materials, selected as scaffolds. In particular, the material, containing calcium compounds, are characterized by ability to hold molecules of nucleic acids by means of complex formation, implemented, probably, according to the mechanism of donor-and-acceptor (coordinative) bond. This mechanism is used in chromatographic columns during purification of nucleic acids. See Giovannini R, Freitag R. Comparison of different types of ceramic hydroxyapatite for the chromatographic separation of plasmid DNA and a recombinant anti-rhesus D antibody. Bioseparation. 2000; 9(6):359-68, incorporated herein by reference in its entirety. The same principle is extrapolated to formation of gene-activated materials, using matrices, containing calcium phosphates. See Bozo I. Ya., Deev R. V., Drobyshev A. Yu. et al. Efficiency of the gene-activated osteoplastic material based on octacalcium phosphate and plasmid DNA with gene vegf for compensation of "critical" and bone defects. N.N. Priorov Information Bulletin of Traumatology and Orthopedics 2015; 1:35-42, incorporated herein by reference in its entirety. However, samples of different production series and even within one series, may considerably differ by the amount of their binding nucleic acids and it is impossible to predict and control the average number, as it is calculated through experiments by combining each matrix variant with nucleic acid.

Fourth, the most important condition of implementation in the clinical practice of any implanted medical product, including gene-activated materials, is sterility. Sterilization is required at the final stage of most medical products manufacturing technology. But all sterilization methods are aimed at elimination inclusive of nucleic acids, which, in case of gene-activated materials, are the main differentiating component of the product, ensuring its primary mechanism and therapeutic effect. In case of gene therapy products, such as "Neovasculgen" (PJSC "Human Stem Cells Institute"), due to absence of scaffold in their composition, the sterile microfiltration is implemented. But the problem of the sterile gene-activated material has not been solved by up to present. In each separate case, the developers have to search for appropriate variants.

Two first described disadvantages predetermine less expressed efficiency of gene-activated materials in tissue regeneration compared to theoretically possible one. Two latter problems primarily predetermine economic expenses and prevent from implementation of gene-activated materials a medical product into the clinical practice.

Considering all above mentioned our efforts were aimed at research and development to make optimized gene-activated materials without mentioned above disadvantages.

BRIEF DESCRIPTION OF THE DRAWINGS

This application file contains at least one drawing executed in color. Copies of this patent application publication with color drawing(s) will be provided by the Office upon request and payment of the necessary fee.

DETAILED DESCRIPTION OF THE INVENTION

Figure 1A:
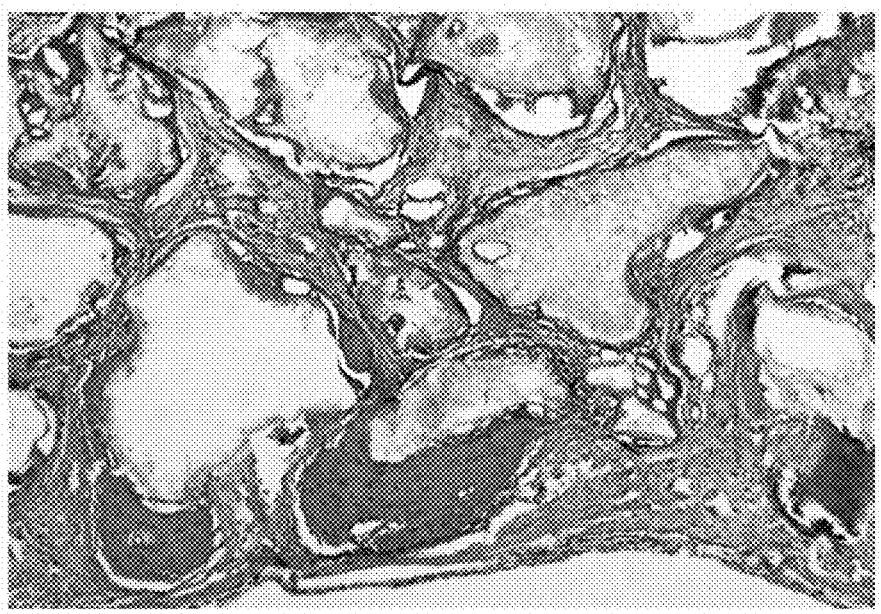
FIG. 1A shows the effects of ordinary gene-activated material on graft in the central zone of the rabbit parietal bone defect thirty days after implantation of materials. Painting: Haematoxylin and eosin. Mag.: x40.

The performed research of gene-activated materials were aimed at: increase of the minimum dose of nucleic acids within the composition of the gene-activated material; providing standard composition of the gene-activated material by accurate reproduction of the selected dose of nucleic acids in each product ample of each series; correction of dynamics of gene structure release from the scaffold composition according to reparative process staging; development of sterile gene-activated material preparation method, including solid scaffold.

The main matter of the invention is development of three methods of optimized gene-activated material production. Within the context of this research, the term "optimized gene-activated material" implies the product, consisting of the scaffold and nucleic acid; at least two of four above mentioned tasks were solved by development of such a material.

Optimized gene-activated materials with two fractions of nucleic acids. The first method deals with gene-activated materials with the scaffold, containing, at least, a part of solid material, its elements are able to hold (bind) molecules of nucleic acids in a transient manner. The list of such matrices includes, but not limited by the following groups: hydroxyapatite, calcium phosphates, bone matrix, obtained using various processing technologies, etc.

As it was noted above, up to present it has not been possible to predict and control the dose of gene constructs for such materials, the effective methods of this dose increase have not been developed. Each variant of the material from the above mentioned groups, separately or within the complex of other additional components (collage, gelatine, alginates, agarose, organic acid polymers, etc.) is able to bind a certain amount of nucleic acids that may considerably differ among samples of scaffold of one and the same composition, even of one series.

We managed to develop the first method of optimized gene-activated materials production, nucleic acids within their composition were divided in two fractions. The first one, bound with the scaffold, probably, by the expense of complex formation with calcium compounds. The second fraction of nucleic acids, unbound, is located on the solid scaffold surface.

The Developed Method Includes the Following Stages:
1. Development of the primary complex "scaffold—nucleic acid" in the following variants: a) synthesis of the scaffold, able to bind on its surface nucleic acid with further combination with at least one molecule of nucleic acid; b) addition of at least one molecule of nucleic acid in the initial materials in the process of the scaffold synthesis (it is practicable for the materials, having a liquid or gel form at one of the production stages). The specified two technological variants of the primary complex production are not mutually exclusive. In particular, after implementation of variant "b" the obtained scaffold with gene constructs may be combined with additional amount of nucleic acids according to variant "a".
2. Arrangement on the obtained primary complex "scaffold—nucleic acid" surface of at least one additional molecule of nucleic acid by a physical method, making it possible to provide such arrangement without formation of chemical bond between the specified scaffold and additional nucleic acid. This stage is critically significant differentiating feature of the developed method, as it allows increasing the total dose of nucleic acids up to the required level.

The second stage may be implemented only for solid scaffold. Enhancement of efficiency and amount of nucleic acids, located on the surface of solid materials without formation of chemical bonds with them, depends on the total surface area, its macro- and microrelief, hydrophilic, sorptive properties of the scaffold and other factors. By modification of the specified factors, it is possible to increase the amount of gene constructs, located on the scaffold surface.

To implement the second stage, use of nucleic acids in water solution (water, various phosphate or other buffer solutions) is the most acceptable option. For more effective arrangement of unbound fraction of nucleic acids on the scaffold surface, pharmaceutically acceptable auxiliary substances may be added in solutions of nucleic acids; they are: glucose, dextrose, sodium hydrogen phosphate dodecahydrate, sodium dihydrogenphosphate dihydrate and any other substances, correcting the scaffold and nucleic acid surface charge, functionalizing the surface and those, intended for holding the molecule on it, and ensuring the primary arrangement of nucleic acids for further attachment on the surface under the impact of physical methods and without formation of chemical bonds. Besides, pharmaceutically acceptable substances provide stabilization of nucleic acids, thus, increasing storage periods.

The list of such physical methods is represented, but not limited by: drying at all acceptable temperature, humidity, medium gas composition, pressure, exposure time, low-temperature impact, ultrasound, magnetic and electrical fields, etc.

Developing this method, we counted, primarily, on the accuracy of dosing and increase on minimum possible concentration of nucleic acids within the gene-activated material composition.

The following 10 variants of solid products were selected for research as scaffolds: xenogeneic demineralized bone matrix—"Biomatrix" (Konektbiofarm LLC, Russia); allogenic demineralized bone matrix—"Perfoost" (N.N. Priorov National Medical Research Centre of Traumatology and Orthopedics, Moscow), "Osteomatrix" (Konektbiofarm LLC, Russia), "Alloplant" (Federal State Institution Russian Eye and Plastic Surgery Center, Ufa); xenogenic deproteinized bone matrix—"Bio-oss spongiosa" (Geistlich, Switzerland); composite material from synthetic hydroxyapatite and xenogenic collagen—"Kolapol—KP3" (Research and Production Company "Polystom", Russia); β-tricalcium phosphate—"Cerasorb" (Curasan, Germany), "Chronos" (Synthes, Switzerland), "TriCaFor" (BioNova, Russia); octacalcium phosphate (OCP, A. Baikov Institute of Metallurgy and Materials Science, Russian Academy of Sciences, Moscow).

As gene constructs the highly-purified supercoiled plasmid DNA carrying gene of VEGF (pCMV-VEGF165) was used. The specified gene structure is an active substance of medical product "Neovasculgen" (PJSC "Human Stem Cells Institute", RU LP-000671 dated 28 Sep. 11), containing dextrose monohydrate as adjuvants—60.0 mg (ND 42-1 1395-07), sodium hydrogen phosphate dodecahydrate—3.94 mg (GOST 4172-76), sodium dihydrogenphosphate dihydrate—0.160 mg (GOST 245-76). The medical product is produced in the form of white lyophilized powder in sterile glass medicine bottle, containing plasmid DNA 1.2 mg and intended for treatment of patients suffering from chronic lower limb ischemia of 2a-3 level according to Fontaine's classification in modification of A. V. Pokrovsky.

The combination of above mentioned scaffolds and gene constructs was performed according to developed original protocol, described in patent of RF N° 2519326 that was partially modified. Contents of the main stages of laboratory protocol:
1) Scaffold washing. Samples of standard mass (100 mg) were incubated in 0.5 M phosphate buffer in the volume of 1 ml at 37° C. with constant shaking during 10 hours.
2) Balancing. The samples were washed using 10 mM phosphate buffer in the volume of 1 ml at 37° C. and with constant shaking 4 times during 10 minutes.
3) Drying. The samples were conditioned at 37° C. until complete drying during 10 hours.
4) Combination of the scaffold and gene constructs. The solution of plasmid DNA (in concentration of 1 μg/μl) was applied in the volume of 0.5 ml on the scaffold samples.

The materials were incubated at 37° C. and with constant shaking during 10 hours.
5) Washing. The samples were washed, using 5 mM phosphate buffer in the volume of 1 ml 3 time, thus, making it possible to remove plasmid DNA, unbound with matrix carrier, from the solution.
6) Drying. The samples were conditioned at 37° C. until complete drying during 10 hours.

For each material 4 replications were made. Results—the amount of plasmid DNA, bound with the scaffold was estimated after its dissociation (treatment with 0.5 M solution of phosphate buffer in the volume of 200-600 μl) at 37° C. and constant shaking during 10 min.) with determination of nucleic acids concentration using fluorometer Qubit 2.0 (Invitrogen, USA).

It was determined that all materials, selected for the research, were able to bind a certain amount of nucleic acids. Most likely, the bond was realized by means of complex formation between calcium compounds included in the composition of matrices and plasmid DNA. But different materials, even within the limits of one group β-tricalcium phosphate, demineralized bone matrix) differed considerably by the amount of nucleic acids they were holding (table 1). It agree completely with the above mentioned peculiarities and disadvantage of currently developed solid gene-activated materials.

TABLE 1

Amount of plasmid DNA, connected with different matrix carriers.

| Item No. | Materials | Concentration of bound plasmid DNA, ng/mg | | | | | |
|---|---|---|---|---|---|---|---|
| | | M | Me | σ | LQ | UQ | IQR |
| 1 | Biomatrix | 67.15 | 67.34 | 6.74 | 61.37 | 72.93 | 11.56 |
| 2 | Perfoost | 19.46 | 19.48 | 1.87 | 17.89 | 21.03 | 3.15 |
| 3 | Osteomatrix | 47.74 | 48.47 | 7.92 | 41.37 | 54.10 | 12.73 |
| 4 | Alloplant | 48.35 | 48.72 | 7.86 | 41.65 | 55.05 | 13.40 |
| 5 | Bio-oss spongiosa | 68.44 | 68.98 | 2.24 | 67.00 | 69.89 | 2.89 |
| 6 | Kolapol-KP3 | 118.12 | 118.06 | 2.24 | 116.21 | 120.04 | 3.83 |
| 7 | Cerasorb | 48.15 | 48.07 | 1.09 | 47.23 | 49.07 | 1.84 |
| 8 | TriCaFor | 32.69 | 32.70 | 1.31 | 31.68 | 33.71 | 2.03 |
| 9 | Octacalcium phosphate | 52.74 | 52.86 | 1.76 | 51.48 | 54.01 | 2.54 |
| 10 | ChronOS | 45.97 | 46.12 | 2.29 | 44.11 | 47.83 | 3.72 |

Note:
M—mean value, Me—median, σ—standard deviation, UQ—upper quartile, LQ—lower quartile, IQR—interquartile range; OCP—octacalcium phosphate.

At the second stage of this research, in order to increase the level of nucleic acids in the composition of gene-activated material and their accurate dosage in the amount of 100, 300 and 500 μg per 1.0 g, shown in table 1, materials, the production technology was modified:
- combination of scaffold with gene constructs was performed right in the solution with target concentrations of nucleic acids (100, 300 and 500 μg per 1.0 g of the scaffold), the solution also contained 10 mM phosphate buffer and 60.0 mg of dextrose monohydrate, incubation was performed during 4 hours;
- the stage of further washing was canceled—right after incubation materials were not removed from the solution, but were put in a lyophilizer;
- lyophilization was performed according to various protocols (basic parameters varied) during 4 days, but the results did not differ considerably.

After application of this method, lyophilized gene-activated materials were incubated, first using 0.9% solution of NaCl with determination of the amount of unbound fraction of plasmid DNA in the solution, and then, after washing of material samples with 0.9% solution of NaCl until obtaining wash water with zero content of plasmid DNA and drying at 37° C., were incubated with 0.5M phosphate buffer solution for dissociation of bound fraction of plasmid DNA.

It was determined, that the total dose of plasmid DNA in all cases corresponded strictly to the specified level—100, 300 or 500 μg per 1.0 g. The amount of bounded fraction of nucleic acids was similar to that, earlier shown for used matrix carriers and presented in Table 1. The amount of unbound fraction was, accordingly, equal to the difference between the target concentration and the bound fraction level.

Thus, the developed method allowed solving two out of four above mentioned tasks: increase of the minimum dose and dosing accuracy. In our research, lyophilization was used for arrangement of unbound fraction of nucleic acids on the solid scaffold surface, which preliminarily bound the maximum possible amount of nucleic acids. At this, it is obvious, that other physical methods may be used to achieve this: exposure at high or low temperatures with various duration, ultrasound and electrophoretic methods, etc.

But the technical result of the developed method and obtained, using it, optimized gene-activated materials was not limited only by dose accuracy and its increase by the required level. Unexpected results were obtained during further research of developed optimized gene-activated materials in orthotopic conditions in vivo.

Figure 1B:
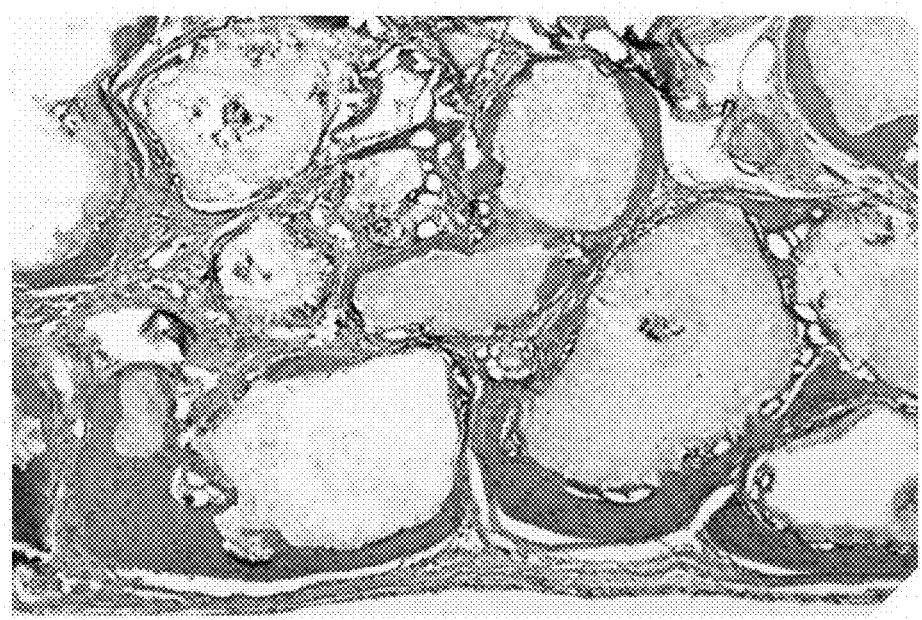
FIG. 1B shows the effects of optimized gene-activated material with two fractions of nucleic acids thrity days after implantation of materials. Painting: Haematoxylin and eosin. Mag.: x40.
Figure 2:
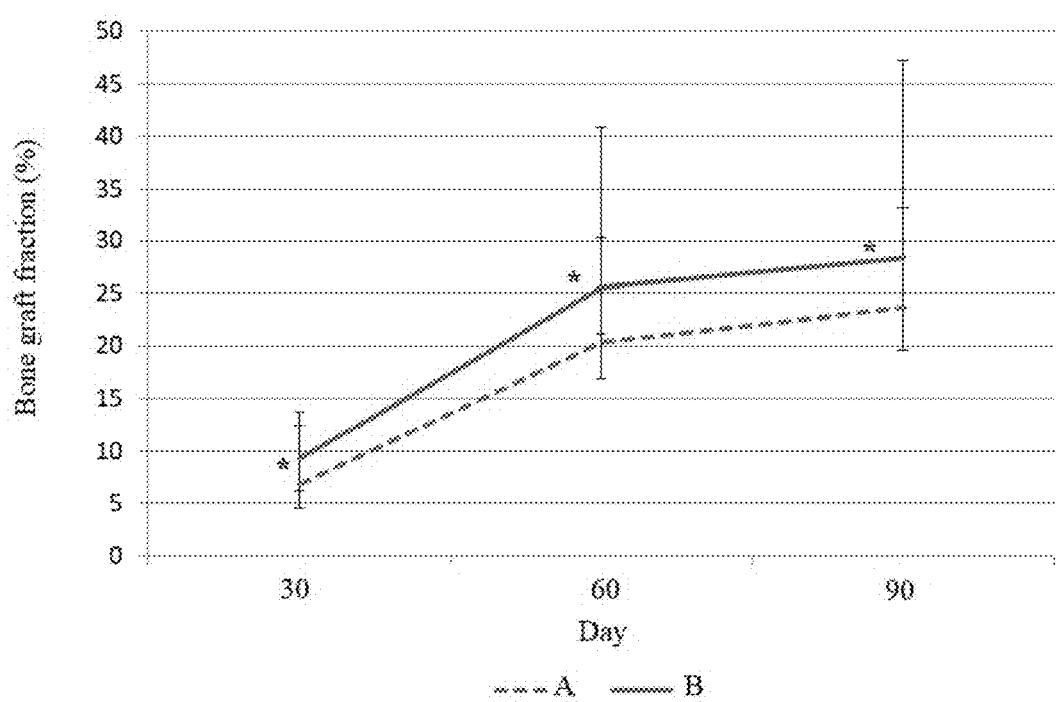
FIG. 2 shows the part of bone graft in the central zone of bone defects in thrity to ninety days after implantation of ordinary gene-activated material (A, dotted line) and optimized gene-activated material with two fractions of nucleic acids (B, solid line). *Differences between groups are statistically significant, $p<0.05$.

The research in vivo was conducted on Chinchilla male rabbits, weighing 2.0-2.5 kg, complying with international regulation of laboratory animal welfare. Each animal underwent two identical symmetrical full-thickness defects of both parietal bones, each 10 mm in diameter, which are "critical" for rabbits, as natural recovery process without any optimizing effect does not complete by defect replacement with a newly formed bone tissue. Earlier, we already obtained and published data about effect of ordinary gene-activated materials that is, containing only one bound fraction of nucleic acids, on bone tissue regeneration in this standard experimental model. As scaffold in those early research three materials from Table 1 were used, with which the highest amount of plasmid DNA with VEGF gene got bound, with minimum variability indicator (Kolapol—KP3, Bio-oss spongiosa, OCP). See Deev et al. (2013); and Bozo et al. (2015). However, comparing the results with the data, obtained in the process of evaluation in the same experimental model of gene-activated materials, containing similar scaffold, but with presence of two fractions of plasmid DNA with VEGF gene, the considerable difference was revealed. It appeared, that optimized gene-activated materials caused formation of statistically significant more volume of bone graft in the central zone of bone defect, that is, in the zone, where fragments of implanted material, but not parietal bone edges, are the source of reparative osteogenesis. FIG. 1 shows the graft in the central zone of the rabbit parietal bone defect, 30 days after implantation of materials: A—ordinary gene-activated material; B—optimized gene-activated material with two fractions of nucleic acids. Painting: Haematoxylin and eosin. Mag.: x40. FIG. 2 shows the part of bone graft in the central zone of bone defects in 30-90 days implantation of materials: A—ordinary gene-activated material; B—optimized gene-activated material with two fractions of nucleic acids.

*Difference differences between groups are statistically significant, p<0.05.

Probably, higher efficiency of developed optimized gene-activated materials was caused by two reasons. First, originally higher dose of gene constructs in the product composition (100, 300 and 500 μg per 1.0 g of scaffold). But considering the fundamental data of dynamics and stage of reparative process, we found out another probable reason. As it was mentioned above, the beginning and achievement of the maximum level of transgene expression after implantation of material in vivo in case with ordinary gene-activated materials are somewhat lagging behind relative to implementation of the reparative process stages. At this, cambial cells, fibroblasts and their precursors migrate in the defect zone much earlier, at the proliferating inflammation stage, that is at the first stage of reparative process (5-6 days after implantation in vivo). Thus, at the early stage, after introduction of the material in the defect zone, there are already a pool of cells-recipients of gene constructs (prefibroblasts, fibroblasts, macrophages) and a population of target cells for the therapeutic protein, coded by the gene structure (cells of main programmed differentiations of injured tissue, endotheliocytes and their precursors). In this regard, unbound fraction of the optimized gene-activated material releases from the scaffold surface right after implantation, forming the first loading dose, which, in its turn, ensures the early peak of transgene expression, falling for the proliferating stage of the inflammation. The second fraction, connected with the scaffold, releases gradually, with its degradation, forming the second prolonged maximum level of the therapeutic protein production into the second regenerative stage of the recovery process. Thus, the optimized gene-activated material, containing two fractions of nucleic acids, begins to have its biologically active effect in the tissue defect zone much earlier, than ordinary gene-activated material, allowing the first one to accelerate the reparative regeneration of tissues.

Regardless of the type of gene structures, intended for arrangement on the scaffold surface, composition of solutions, containing these nucleic acids, composition of auxiliary substances, physical methods, ensuring transient attachment of gene structures on the scaffold surface and modifications of scaffold surface properties, the differentiating feature of developed method and products is absence of chemical bond between the second fraction of nucleic acid and scaffold with presence of the first fraction of nucleic acid, bound with it. The presence of two fractions, bound and unbound ones, is the main differentiating feature of the developed products compared to other known gene-activated materials. See Methods of gene transfer in vivo, incorporated herein by reference in its entirety.

Example 1

Using the developed method, we produced a number of variants of optimized gene-activated materials, containing two fractions of nucleic acids (bound and unbound ones) (Table 2).

TABLE 2

Variants of production of optimized gene-activated materials, containing two fractions of nucleic acids.

| Item No. | Scaffold | Gene structures, amount (M ± σ) per 1 mg of the matrix carrier | |
|---|---|---|---|
| | | Bound fraction | Unbound fraction |
| 1 | β-tricalcium phosphate* | 32.69 ± 1.31 | 167.31 ± 5.48 |
| 2 | Octacalcium phosphate* | 52.74 ± 1.76 | 47.26 ± 3.50 |
| 3 | Xenogenic bone matrix* | 68.44 ± 2.24 | 231.56 ± 2.79 |
| 4 | Allogenic bone matrix* | 48.35 ± 7.86 | 251.65 ± 4.31 |
| 5 | Co-polymer of lactic and glycolic acids** | 50 ± 1.06 | 50 ± 2.31 |
| 6 | Collagen + hydroxyapatite* | 118.12 ± 2.24 | 281.88 ± 6.25 |
| 7 | Collagen + hydroxyapatite** | 100 ± 3.37 | 200 ± 7.49 |
| 8 | Collagen + hydroxyapatite*** | 229 ± 5.94 | 271 ± 6.42 |

*Production of scaffold with further combination with nucleic acids of bounded fraction
**addition of nucleic acids of bound fraction at the stage of the scaffold synthesis
***addition of nucleic acids of the first part of the bound fraction at the stage of the scaffold synthesis with its further combination with nucleic acids of the second part of the bound fraction.

Figure 3A:
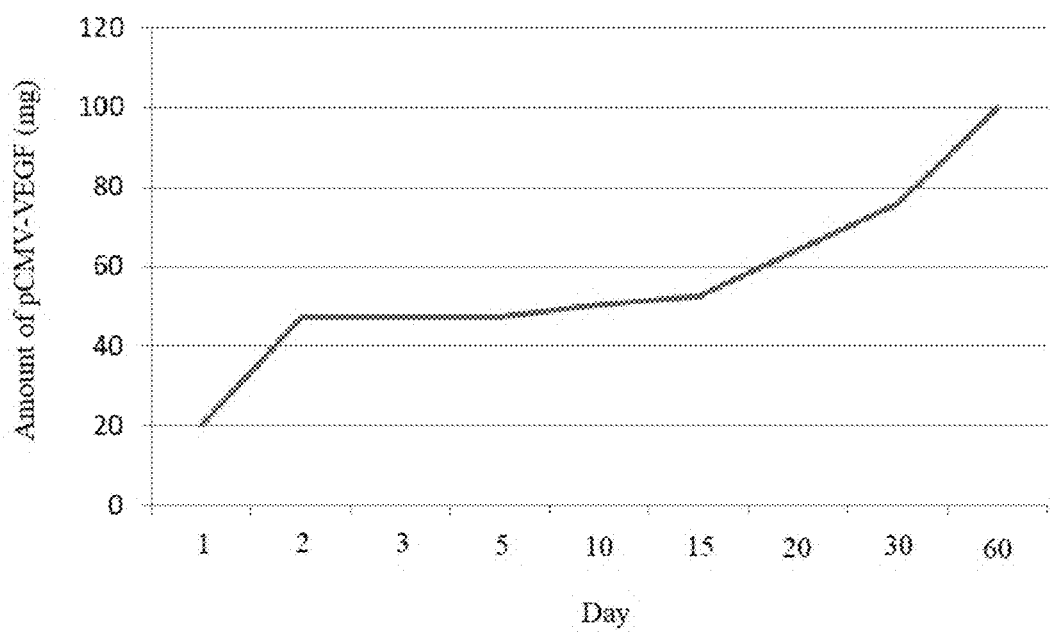
FIG. 3A shows dynamics of nucleic acids release (pCMV-VEGF) from the structure of gene-activated material that is: optimized gene-activated materials with two fractions of nucleic acids.
Figure 3B:
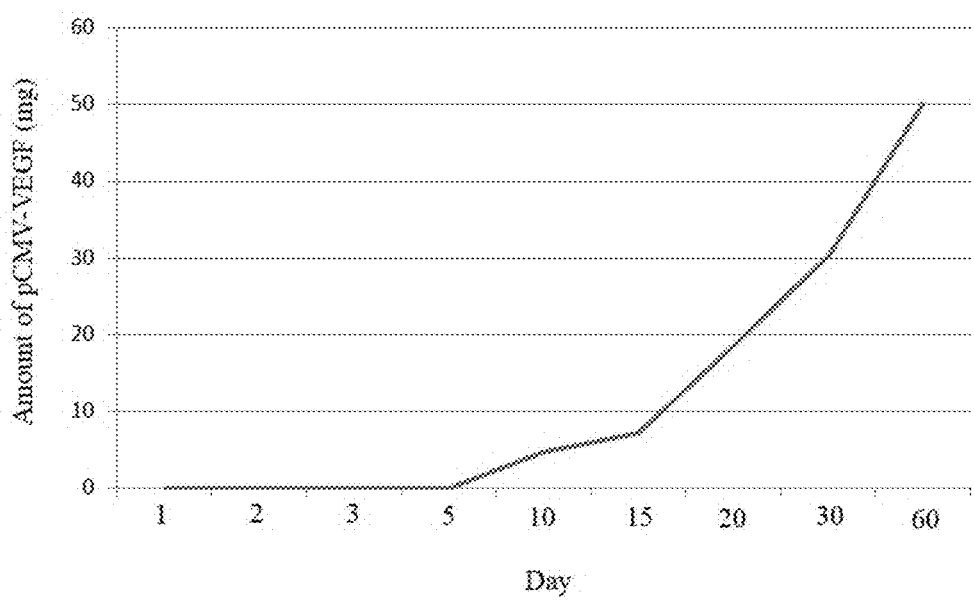
FIG. 3B shows dynamics of nucleic acids release (pCMV-VEGF) from the structure of gene-activated material that is ordinary gene-activated material.

The developed optimized gene-activated materials were studied in vitro in order to plot a curve of gene constructs release. The result, typical for all obtained by us gene-activated materials with two fractions of nucleic acids, compared to ordinary gene-activated materials is shown in FIG. 3. The research was performed in standard model condition without evacuation/destruction of nucleic acids, released into the solution, that is, the accumulated concentration in the solution was determined. FIG. 3A shows dynamics of nucleic acids release (pCMV-VEGF) from the structure of gene-activated material that is: optimized gene-activated materials with two fractions of nucleic acids.

It is important, that the developed method allows using any solid scaffold and nucleic acids for formation of optimized gene-activated materials, suggesting approach flexibility and predetermines significant perspectives for implementation in the clinical practice for various situations (regeneration of tissues and organs of musculoskeletal system, skin, mucous membrane, heart-vascular system organs, peripheral nerves, hollow and parenchymal organs, etc.).

By application of various variants of gene constructs, including those, coding various transgenes, optimized gene-activated materials, fractions of nucleic acids with different compositions of vector and (or) transgene (-s) may be produced. In particular, for preparation of products, shown in Table 2, we used not only plasmid DNA, carrying VEGF gene, but also plasmid DNA, carrying genes of other proteins: factor of stromal cells-1 (SDF-1), main growth factor of fibroblasts (bFGF), neuralizing growth factor (NGF), epidermal growth factor (EGF), bone morphogenetic proteins (BMP), interleukins (IL), etc.), including combinations of genes of several proteins (SDF-VEGF; BMP-VEGF, etc.) and in various combinations.

For production of optimized gene-activated materials other gene constructs, coding any other proteins, may also be used, including cytokines, membrane and cytoplasmic receptors, transcriptional factors, etc., depending on the biological effect to be achieved by application of the gene-activated material. The selection is also determined by the required dynamics of the biological effect development.

For instance, we used optimized gene-activated material, consisting of OCP, bound fraction of nucleic acids in the form of plasmid DNS with VEGF gene and unbound fraction in the form of two-carrier plasmid DNA with genes VEGF and SDF. This selection was based on the necessity to attract a considerable number of cambial reserves (cells-precursors of osteoblasts and endotheliocytes) into the bone defect zone as soon as possible after implantation, including system sources. For this part of the action mechanism the unbound fraction of two-cassette plasmid DNA was responsible, as SDF is a known inducing substance of cell homing. At the regeneration stage the effect on the cells-precursors, already attracted in the defect zone, angiogenesis activation, in particular. This biological effect was realized by means of the bound fraction of gene constructs—plasmid DNA with VEGF gene,—which gradually released from the scaffold structure, with its biodegradation, and activated its action mechanism.

The specified example is only a variant of successful use of the developed method of production of optimized gene-activated materials. Variation of composition of two fractions of nucleic acids may make it possible to achieve complex biological effects, different in implementation time by difference in dynamics of release of two fractions of nucleic acids and by its character by possible use of various gene constructs within the composition of two fractions.

Thus, optimized gene-activated materials, containing two fractions of nucleic acids (bound and unbound) are characterized not only by the dose accuracy and possibility to increase up to the required level, but also allows to perform more subtle and complex effect on the reparative process, achievable, using ordinary gene-activated materials.

Optimized gene-activated materials, containing functionalized scaffold One of the other directions, developed by us, allowing obtaining optimized gene-activated materials, consists in increase of the minimum dose and dosing accuracy of the bound fraction of nucleic acids by modification of the scaffold.

As it was mentioned above, solid materials, containing calcium compounds, are able to bind a certain amount of molecules of nucleic acids by means of complex formation, implemented, probably, according to the mechanism of donor-and-acceptor (coordinative) bond. Revealing of this effect, which is primarily applied in chromatography, lead to attempts of hydroxyapatite composition modification, used in chromatographic columns, by other metals, such as strontium. See Kawasaki T, Niikura M, Takahashi S, Kobayashi W. Strontium-phosphate hydroxyapatite high-perfoiinance liquid chromatography. Biochem Int. 1987 December; 15(6): 1 137-49, incorporated herein by reference in its entirety. Besides, there are precedents of calcium phosphate matrices by other metals, such as magnesium, to change the material physical and chemical properties and optimization of their use as scaffold for the cells within the composition of tissue-engineered products. See Zhang J, Ma X, Lin D, Shi H, Yuan Y, Tang W, Zhou H, Guo H, Qian J, Liu C. Magnesium modification of a calcium phosphate cement alters bone marrow stromal cell behavior via an integrin-mediated mechanism. Biomaterials 2015 June; 53:25 1-64, incorporated herein by reference in its entirety.

However, up to present, the modification of the material, containing calcium compounds, by complexing compounds for further binding with nucleic acids and preparation of the gene-activated material has not been developed.

The method, we developed, includes the initial material treatment, which was planned for further synthesis of scaffold, salt (-s) solutions of other metals—complexing compounds (in particular, strontium, barium, magnesium) with chemical reaction initiation, leading to obtaining of the material, containing calcium compounds and compounds of other metal-complexing agent. The scaffold, obtained, using this method, is to be combined with nucleic acids to prepare the optimized gene-activated material.

By simultaneous or subsequent treatment of the original material, using salt solutions of various metals, several different complexing compounds may be added in various ratios.

Increase of the minimum dose of gene constructs and dose accuracy are provided by variability of the experimentally calculated amount, composition and ratio of the complexing compound, introduce in the scaffold composition.

Example 2

Using the developed method, from tricalcium phosphate (TCP) ($Ca_3(PO_4)_2$) with atomic ratio of elements Ca/P 1.5±0.1 the material from octacalcium phosphate (OCP) was synthesized, where from 1 to 3% $Ca^{2+}$ were replaced by $Mg^{2+}$, $Sr^{2+}$ and $Ba^{2+}$ in various ratios.

The specific feature of this variant of production of optimized gene-activated materials was a balanced integration of the original material treatment stage of a complexing compound solution in the known stage of OCP synthesis. See "Method of ceramics production based on octacalcium phosphate". International filing date: 31, Aug. 2016. International application number: PCT/RU20 16/0005 87, incorporated herein by reference in its entirety. In other words, the scaffold functionalization was performed during its synthesis, not as an additional stage. Depending on the material nature, any variant is possible.

TCP modification was performed in special buffer solutions A and B. To prepare solution A, water solution 1.5 M of sodium acetate and solution of 0.15±0.02 M glutamic amino acid were prepared and brought to value pH 5.5±0.1 of solution, using orthophosphoric acid. See "Method of ceramics production based on octacalcium phosphate". (2016). Sodium acetate serves as a buffer. To obtain solution B, water solution 1.5 M of sodium acetate and magnesium acetate, strontium or barium with value pH 8.7±0.1 of solution. Solution A is used to transform TCP into dicalcium phosphate dihydrate (DCPD). The process is conducted at 35±1° C. TCP scaffold and solution A ratio is 1:100. The process of TCP transformation into DCPD is complete within 7 days. If the process is conducted at temperature higher than 35±1° C., together with DCPD, dicalcium phosphate (DCP) starts to form and it is cytotoxic. At temperature below 30° C. reaction of transition becomes slower; in a month of conditioning in the solution, the value less than 50% of DCPD is reached. Then the obtained matrix carriers were washed in distilled water until pH value was not lower than 6.5, then they were dried at 35±1° C. during one day.

Solution B serves for transformation of DCPD into OCP. Chemical treatment shall also be performed at 35±1° C. DCPD and solution B ratio is 1:100. The process of DCPD transformation into OCP is complete within 7 days. In this process, simultaneously with transformation of DCPD into OCP, a partial cationic replacement $Mg^{2+}$, $Sr^{2+}$, $Ba^{2+}$, $Ca^{2+}$ is implemented, that is, formation of positively charged complexes in the process of apatite structure formation (DCPD→OCP), which is also a differentiating feature of this technology compared to the one, described in "Method of ceramics production based on octacalcium phosphate". (2016). When 1-3% of calcium ions are replaced for $Mg^{2+}$, $Sr^{2+}$ or $Ba^{2+}$, one-phase replaced OCP is formed. Increase of metal ions content in the solution causes inhibition of DCPD into OCP hydrolysis process, that is caused by effect of metal ions on processes of "deposition—solution" of DCPD.

It should be noted, that this method may be used at physiological temperatures (not exceeding 40° C.), that is quite important for synthesis and functionalization of such scaffold as OCP (thermally unstable compound).

Scaffold, modified by complexing compound, were combined with nucleic acids (in particular, plasmid DNA with VEGF gene) according to the method, described in RF N° 25 19326 and partially modified method, described above.

The production method of optimized gene-activated materials, containing scaffold, functionalized by complexing compounds, made it possible to develop products from OCP with minimum concentrations of gene constructs, exceeding by 1.2-2.3 the amount of nucleic acids, bound with standard OCP (Tables 1 and 2).

But unexpected data were obtained, when plotting a curve of gene constructs release from obtained optimized gene-activated materials and when evaluating efficiency of transfection of cell culture in vitro.

Figure 4:
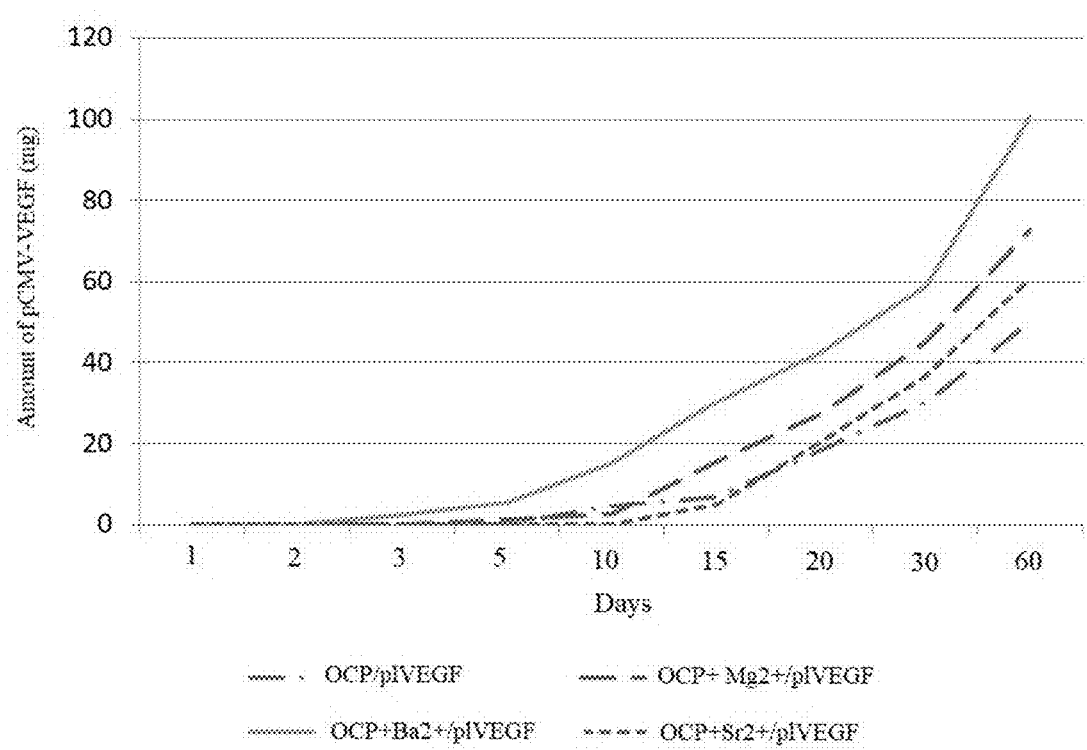
FIG. 4 shows dynamics of gene constructs release from ordinary and optimized gene-activated materials, containing various complexing compounds.

It turned out, that the scaffold functionalization (OCP, in particular), using complexing compound (such as magnesium, barium and strontium) caused change in dynamics of release of gene constructs from the composition of optimized gene-activated materials, compared to standard ones, containing ordinary OCP and nucleic acids (FIG. 4). FIG. 4 shows dynamics of gene constructs release from ordinary and optimized gene-activated materials, containing various complexing compounds.

The probable cause is a different bonding force in metal compound complexes with molecules of nucleic acids. The confirmation of this hypothesis requires performance of additional studies, which will allow in various experimental systems in vitro and in vivo to reveal the dynamics of gene constructs release and program it by changing composition, amount and ration of complexing compound within the scaffold composition.

Figure 5A:
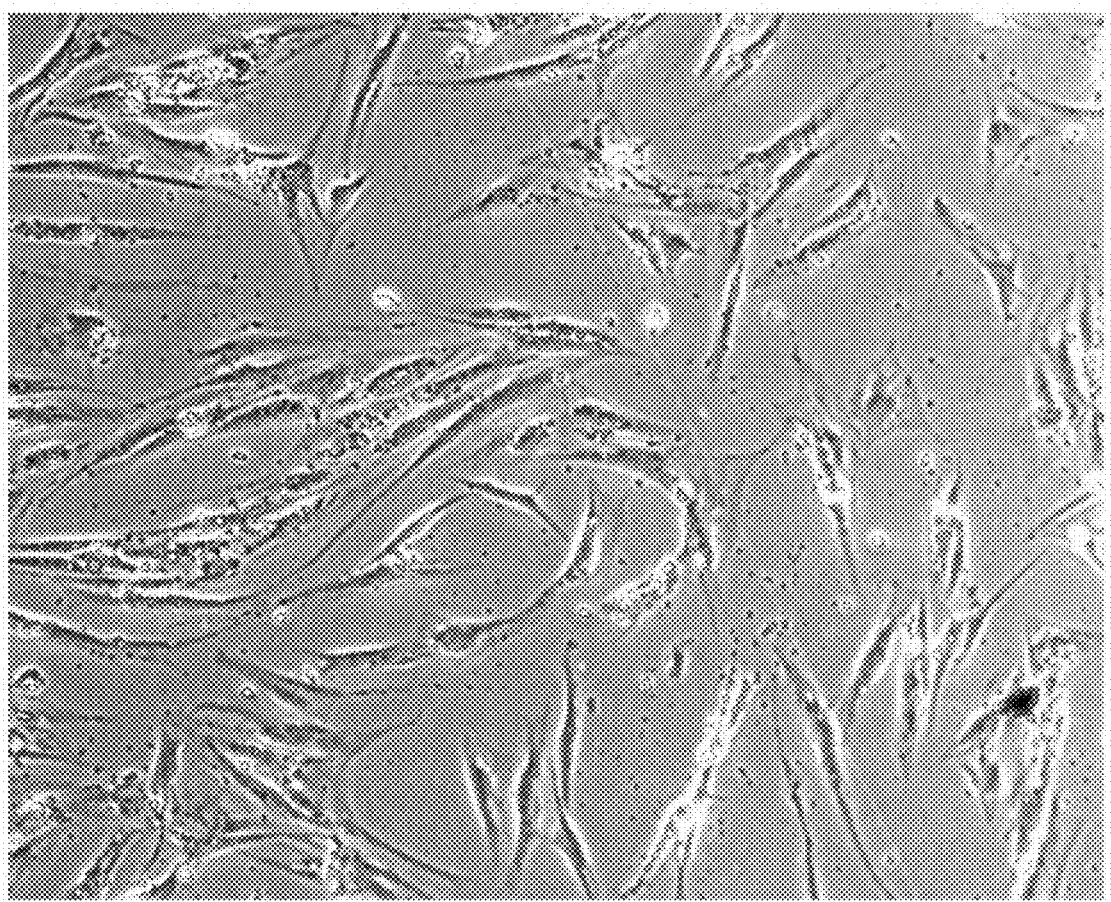
FIGS. 5A-5C depict microparticles of complexing compound phosphates in the bone marrow MMSC, co-incubated with gene-activated materials: OCP/pCMV-VEGF (FIG. 5A); OCP+$Mg^{2+}$/pCMV-VEGF (FIG. 5B); OCP+$Ba^{2+}$/pCMV-VEGF (FIG. 5C).
Figure 5B:
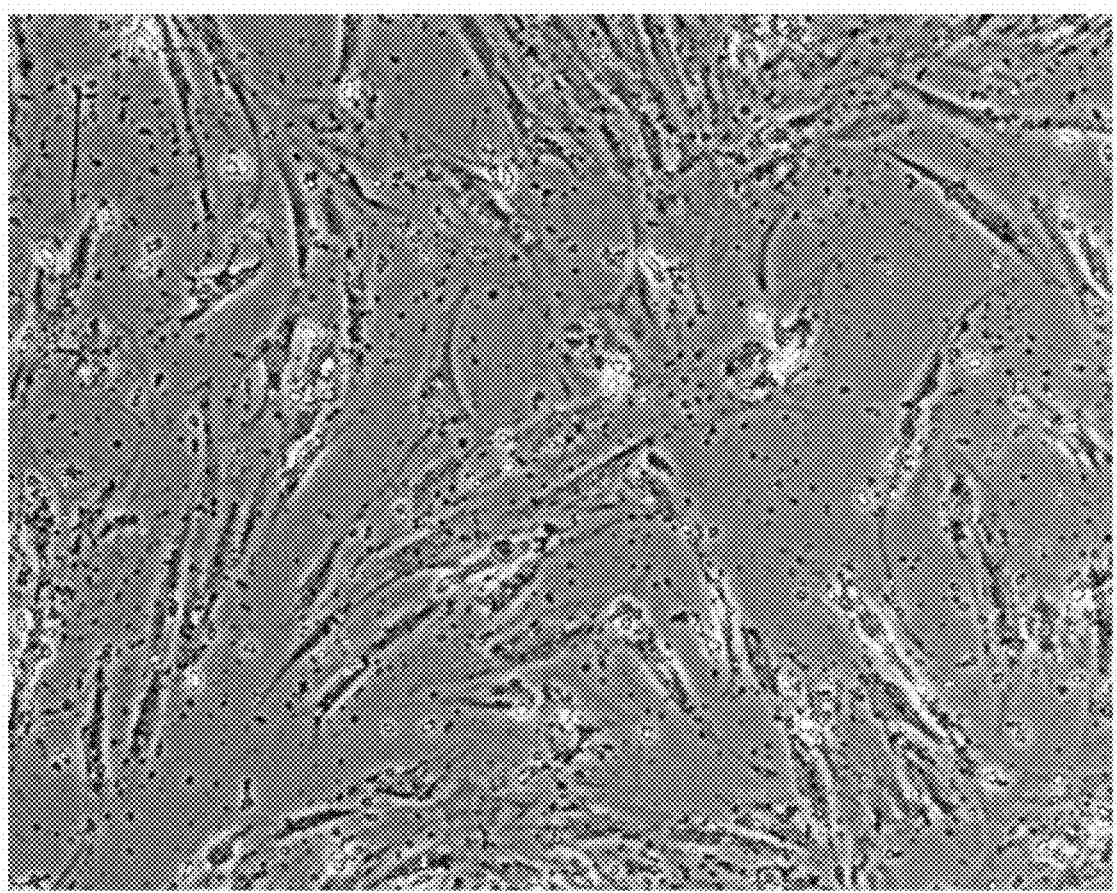
Figure 5C:
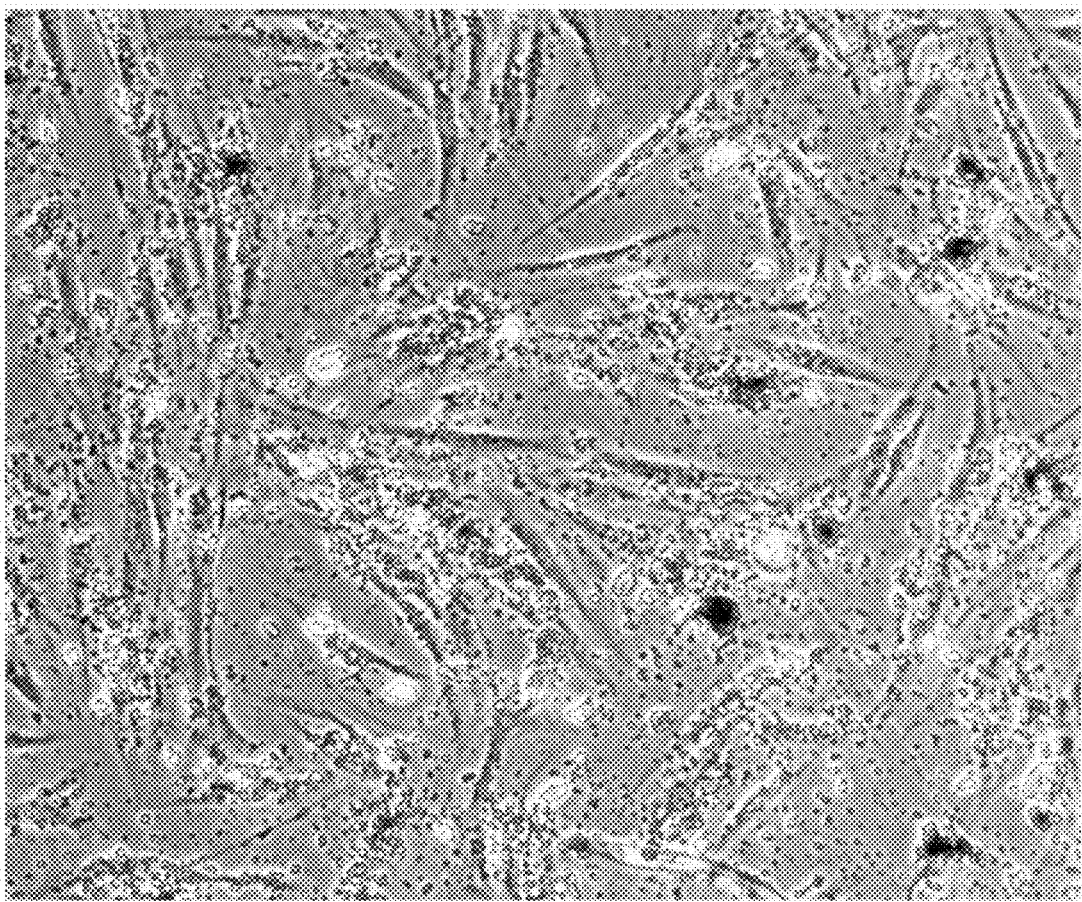

Another unexpected technical result of the developed method is increase of efficiency of cell culture transfection in vitro, co-incubated with optimized gene-activated materials, containing functionalized scaffold from calcium phosphate. The calcium phosphate optimization method of transfection is widely known; it is based on use of calcium chloride and phosphate buffer solutions, forming precipitated calcium phosphates, binding molecules of gene constructs and penetrating into cells by means of endocytosis. See Graham F L, van der Eb A J. Transformation of rat cells by DNA of human adenovirus 5. Virology. 1973 Aug.; 54(2):536-9, incorporated herein by reference in its entirety. Besides, assumptions were made, that gene-activated materials, consisting of calcium phosphates and plasmid DNA, have higher transfection efficiency. See Keeney M., van den Beucken J. J., van der Kraan P. M. et al. The ability of a collagen/calcium phosphate scaffold to act as its own vector for gene delivery and to promote bone formation via transfection with VEGF(165). Biomaterials 2010; 3 1(10): 2893-902, incorporated herein by reference in its entirety. But until present, there have been no data, testifying about increase of transfection level by means of modification of calcium phosphate scaffold, using other complexing compounds. During our research this effect was detected. In in vitro experiment multipotent mesenchymal stromal cells were incubated with ordinary (OCP/pCMV-VEGF) and optimized gene-activated materials (OCP+$Mg^{2+}$/pCMV-VEGF; OCP+$Sr^{2+}$/pCMV-VEGF; OCP+B $a^{2+}$/pCMV-VEGF; OKФ+$Mg^{2+}Ba^{2+}$/pCMV-VEGF), located in inserts «transwelb-system (membrane with pore size 3 μm). In other words, cells and materials were divided by a membrane, permeable for culture medium. Using PCR—RT and EIA, transfection efficiency of optimized gene-activated materials, higher by 1.5-2 times was detected. This effect is caused, most likely, by the material microparticles, detected on the light-optical level in the zone with cells; the microparticles are located extracellularly and intracellularly (FIG. 5). Most likely, these microparticles, less than 3 μm in diameter, represented precipitated calcium phosphates and phosphates of other complexing compounds (magnesium, barium, strontium), which bound molecules of gene constructs and entered cells. Similar to microparticles, detected on the light-optical level, were detected and in case with ordinary gene-activated materials from OCP. But increase of transfection level in case of optimized products may be related to many reasons: higher level of other precipitated complexing compounds, penetrating in the cells, other bonding force with molecules of gene constructs, presence of protective properties of phosphate microparticles of other metal, protecting gene constructs from destruction by cell ferments. These hypothetical reasons of enhanced transfection efficiency require further studies. FIG. 5 shows microparticles of complexing compound phosphates in the bone marrow MMSC, co-incubated with gene-activated materials: A—OCP/pCMV-VEGF; B—OCP+$Mg^{2+}$/pCMV-VEGF; B—OCP+$Ba^{2+}$/pCMV-VEGF.

It should be noted, that the developed method of optimized gene-activated materials production from functionalized scaffold complexing compound and gene constructs may be used in combination with the first method, described in this invention. It other words, to the gene-activated materials, obtained according to the second method, unbound fraction of nucleic acid may be added. In this case, optimization of gene-activated material will be achieved according to two directions: functionalization of the scaffold with increase of dose of the bound fraction of nucleic acids and introduction of unbound fraction of gene constructs. It is obvious, that such complex approach will allow producing even more efficient products, combining advantages of each approach.

Sterile medical product from gene-activated materials. All gene-activated materials, at different stages of experimental studies in Russian Federation and abroad, are prototypes or main components of medical products. Any medical product, intended for implantation into the recipient's organism, shall be sterile. However, all sterilization methods are aimed at destruction of all microorganisms and their components, including nucleic acids as a class of organic substances. But nucleic acids are biologically active differentiating component of gene-activated materials, ensuring their specific action. In this regard, development of sterile medical product from gene-activated material is an extremely difficult task.

In the course of studies we developed technology, allowing to produce medical products from optimized gene-activated materials, using one or both above mentioned methods, but in a sterile condition.

The developed method includes the following stages:
1) formation of initial components: sterile solution of highly-purified nucleic acids (Plasmid DNA with gene encoding VEGF or (and) SDF, other genes and their combinations) and solid scaffold;
2) Treatment of obtained scaffold in the phosphate buffer solution, further sterilization, using an appropriate method (autoclave treatment, ionizing radiation, etc.)
3) introduction of nucleic acids in the solution of phosphate buffer with pharmaceutically acceptable auxiliary substances, ensuring stability of nucleic acids, into sterile container with the specified amount of scaffold in the ratio of not less than 100 ng of nucleic acids per 1 mg of scaffold, incubation shall not be less than 4 hours at optimal temperature (about −37° C.);

4) freeze-drying of the scaffold, bound a part of added nucleic acids in the solution with nucleic acids, the remaining solution from the container or some other solution with nucleic acids may be used for this.

As a sterile container at the third stage of the developed method the container may be used, where produced medical product will be delivered to consumers (medicine bottle, syringe dispenser, etc.). Besides, packing into the specified containers may be performed at the second stage with further sterilization in them. All manipulations at the third stage hall be performed in sterile conditions (class A or B premises).

Lyophilization at the fourth stage shall be performed in sterile conditions according to appropriate protocol. After lyophilization is complete, covers of sterile containers with obtained medical products shall be tightly closed (optimally, using lyophilizer tray right after the process is complete). Closed containers with optimized gene-activated materials may be delivered in sterile conditions in the packaging zone (materials of individual package and marking shall be preliminarily sterilized), if it is required to preserve sterility of the external surface of medical products.

According to the developed method, several variants of medical product from OCP or deproteinized bone matrix and plasmid DNA, encoding various genes (VEGF, SDFf etc.). The results of control studies showed the absolute sterility of medical products.

Embodiments of the invention include but are not limited to the following.

1. The development method of optimized gene-activated material, characterized by accuracy of nucleic acids dosage in its composition and separation of the specified nucleic acids in two fractions by the release rate from scaffold composition. It consists in development of the scaffold, binding at least one molecule of nucleic acid with further arrangement on its surface at least one more molecule of nucleic acid, using a physical method, allowing providing this arrangement without formation of chemical bond between the specified scaffold and additional nucleic acid.
2. The optimized gene-activated material, produced according to embodiment 1, containing, at least, two molecules of nucleic acid, one of which is bound with the scaffold and the other one is located on the scaffold surface, using some appropriate physical method without formation of chemical bond with the scaffold.
3. The method of sterile optimized gene-activated material, consisting of solid scaffold and two fractions of nucleic acids including the following stages:
   formation of initial components: sterile solution of highly-purified nucleic acids and solid scaffold;
   processing of obtained scaffold in 10 mm solution of phosphate buffer; sterilization using a physical method;
   introduction of nucleic acids in the solution of phosphate buffer with pharmaceutically acceptable auxiliary substances, ensuring stability of nucleic acids, into sterile container with the specified amount of scaffold in the ratio of not less than 100 ng of nucleic acids per 1 mg of scaffold, incubation shall not be less than 4 hours;
   freeze-drying of the scaffold, bound a part of added nucleic acids in the solution with nucleic acids, the remaining solution from the container or some other solution with nucleic acids may be used for this.
4. The sterile gene-optimized material, consisting of solid scaffold and two fractions of nucleic acids, prepared according method, described in embodiment 3.
5. The production method of the optimized gene-activated material, consisting in introduction into the scaffold composition at the stage of its synthesis, of any complexing compound by treatment of the initial material with the solution, containing the salt of the complexing compound metal. The complexing compound shall be able to hold the nucleic acid molecule with further combination of the modified scaffold with at least one nucleic acid with obtaining optimized gene-activated material.
6. The optimized gene-activated material, prepared according to the method described in embodiment 5.
7. The optimized gene-activated material, characterized by the modified composition of the scaffold, at least one complexing compound and presence of two fractions, bound and unbound, nucleic acids, prepared by combination of methods, described in embodiment 1 and embodiment 6.

Other embodiments of the invention include the following.

A gene-activated material comprising a scaffold and at least one nucleic acid, wherein the nucleic acid is bound with the scaffold or wherein the nucleic acid is unbound and located on the surface of the scaffold. In some embodiments, the gene-activated material is bound with or within the scaffold, for example, by chemical or covalent bonds. In another embodiment, the gene-activated material contains an unbound nucleic acid located on a surface of the scaffold. In still other embodiments, the gene-activated material may contain both bound and unbound nucleic acids, which may be the same or different, for example, where at least one nucleic acid is bound with the scaffold and at least one second nucleic acid is located on a surface of the scaffold and is unbound to the scaffold. Mixture of nucleic acids, such as a mixture of 1, 2, 3, 4, 5, 6, 7, 8, 9, 10 or >10 nucleic acids may be present in a gene-activated material.

The scaffold of the gen-activated material may comprise, consist essentially or consist of beta-tricalcium phosphate, octacalcium phosphate, or another calcium phosphate. In some embodiments, the scaffold will comprise demineralized bone matrix which may be autologous, allogenic, or xenogenic. In other embodiments the scaffold may comprise a deproteinized bone matrix which may be autologous, allogenic or xenogeneic. The scaffold may be mixture of one or more scaffold materials, such as those described herein or a composite comprising hydroxyapatite and collagen. A scaffold may also comprise a copolymer, such as a copolymer of lactic and glycolic acids.

A gene activated material as disclosed herein may contain one, two, three or more nucleic Acids which may be RNA, DNA or modified forms of RNA or DNA resistant to nucleases compared to unmodified RNA or DNA. One example of a nucleic acid is plasmid DNA, which may be linear or supercoiled. The nucleic acid may encode any protein, such as an enzyme or growth factor, especially those useful for enhancing or modulating bone growth. These include nucleic acids selected from the group consisting of one that encodes VEGF, factor of stromal cells-1 (SDF-1), main growth factor of fibroblasts (bFGF), neuralizing growth factor (NGF), epidemial growth factor (EGF), bone morphogenetic proteins (BMP), interleukins (IL) and combinations thereof.

Another embodiment of the invention involves a method for producing a gene-activated material comprising forming a solution comprising a solid scaffold and nucleic acid, for example at a ratio (wt %) of nucleic acid to scaffold of 10, 25, 50, 75, 100, 200, 300, 400, 500, 600, 700, 800, 900 or 1,000 ng per 1 mg of scaffold, preferably in a ratio of not less than 100 ng of the nucleic acids per 1 mg of scaffold, and incubating the solution for a time and under conditions suitable for association of the nucleic acids with the surface of the scaffold without covalent binding, for example, incubating the solid ranging from 0, 10, 20, 30, 40, 50 or >50 degrees, preferably at about 37° C., for a time ranging from 0.5, 1, 2, 3, 4, or >4 hours. The nucleic acids may be RNA or DNA or modified forms of RNA and DNA, for example, forms that are resistant to degradation by nucleases. After the nucleic acids and solid scaffold have associated, this associated complex may be lyophilized or freeze dried, optionally after removal of unassociated material thereby producing a scaffold comprising unbound nucleic acids on a surface of the scaffold; and/or a complex of chemically or covalently bound nucleic acids with a scaffolding material may be produced by forming a solution comprising substrates for scaffold formation and a complexing compound thereby forming a functionalized scaffold, and mixing the functionalized scaffold with at least one nucleic acid, thereby forming a scaffold comprising a bound nucleic acid. For either method, the materials may be sterilized during or after their production so as to be suitable for medical or surgical use.

Another aspect of the invention is a method for treating a subject in need of bone regeneration or in need of a bone graft comprising implanting the gene-activated material disclosed herein. The treatment may involve administering, injecting or implanting gene-activated material, such as one that comprises at least one nucleic acid is selected from the group consisting of one that encodes VEGF, factor of stromal cells-1 (SDF-1), main growth factor of fibroblasts (bFGF), neuralizing growth factor (NGF), epidermal growth factor (EGF), bone morphogenetic proteins (BMP), interleukins (IL) and combinations thereof. In some embodiments of the method, the at least one nucleic acid is bound with the scaffold and at least An amount of the gene activated material sufficient to enhance bone regeneration or repair may be selected by those skill in the medical arts based on various factors including patient condition, age, sex, etc. In some embodiments the gene-activated material so administered may contain at least 1, 2, 5, 10, 20, 50, 100, 200 or 500 micrograms of nucleic acid per gram of scaffold.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A gene-activated material comprising (i) a solid scaffold comprising a first portion of a predetermined dose of at least one nucleic acid; and (ii) a surface of the solid scaffold comprising a second portion of the predetermined dose of the at least one nucleic acid physically bound to said surface;
wherein the first and second portion together comprise the predetermined dose;
wherein the solid scaffold incorporating the at least one nucleic acid is produced by admixing in solution the at least one nucleic acid with scaffolding materials to produce a primary complex containing nucleic acids that are chemically-bound to the scaffolding materials and that are not removed by washing in a 0.9% solution of NaCl, and then, without washing, lyophilizing the admixture, thereby producing a gene-activated material containing a first-chemically bound fraction of the nucleic acid that is incorporated into the scaffold, which is not removed by washing in a 0.9% solution of NaCl, and a second unbound fraction of the nucleic acid that can be removed from the solid scaffold by washing in a 0.9% solution of NaCl;
wherein the gene-activated material is produced by admixing the predetermined dose of the at least one nucleic acid with scaffolding materials in the presence of beta tri-calcium phosphate to produce a primary complex containing the first portion of the dose of the at least one nucleic acid; and lyophilizing or drying the solution used to prepare the scaffold, thereby producing said gene-activated material;
wherein the scaffolding materials comprise beta tri-calcium phosphate and a complexing agent; and
wherein the at least one nucleic acid is DNA.

2. The gene-activated material of claim 1, wherein the predetermined dose ranges from 100 to 500 μg per gram of scaffold.

3. E gene-activated material of claim 1, wherein the at least one nucleic acid is a plasmid.

4. The gene activated material of claim 1, wherein the solid scaffold further comprises at least one of $Ba^{2+}$, $Mg^{2+}$, and $Sr^{2+}$ as the complexing agent.

5. The gene-activated material of claim 1, wherein the predetermined dose of the at least one nucleic acid is admixed with materials that form the solid scaffold prior to formation of the solid scaffold.

6. The gene-activated material of claim 1, wherein the predetermined dose of the at least one nucleic acid is admixed with the solid scaffold after synthesis of the solid scaffold.

7. The gene activated material of claim 1, wherein the first portion of the predetermined dose of at least one nucleic acid is further hound to the scaffold via complex formation with at least one of $Ba^{2+}$, $Mg^{2+}$, and $Sr^{2+}$; and wherein the second portion of the predetermined dose of at least one nucleic acid is bound to the surface of the scaffold by drying.

8. The gene-activated material of claim 7, wherein the first portion of the predetermined dose of the at least one nucleic acid is complexed with $Ca^{2+}$ and further complexed with at least one of $Ba^{2+}$, $Mg^{2+}$, and $Sr^{2+}$; and wherein said gene-activated material provides an earlier and higher release of the predetermined dose than an otherwise identical gene-activated material not comprising $Ba^{2+}$, $Mg^{2+}$, and $Sr^{2+}$.

9. The gene-activated material of claim 1, wherein the second portion of the at least one nucleic acid is physically bound to the surface of the scaffold in combination with at least one of glucose, dextrose, sodium hydrogen phosphate dodecahydrate, or sodium dihydrogenphosphate dehydrate.

10. The gene-activated material of claim 1 that is sterile.

11. The gene-activated material of claim 1 that is produced by admixing the predetermined dose of the at least one nucleic acid with a solid scaffold that further contains at least one complexing agent selected from the group consisting of $Ba^{2+}$, $Mg^{2+}$, and $Sr^{2+}$, to produce a primary complex containing the first portion of the dose of the at least one nucleic acid; and lyophilizing the solution used to prepare the scaffold, thereby producing said gene-activated material.

* * * * *